United States Patent  
Reggiardo (10) Patent No.: US 8,112,138 B2  
(45) Date of Patent: Feb. 7, 2012

(54) METHOD AND APPARATUS FOR PROVIDING RECHARGEABLE POWER IN DATA MONITORING AND MANAGEMENT SYSTEMS

(75) Inventor: Christopher V. Reggiardo, Castro Valley, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 750 days.

(21) Appl. No.: 12/239,047

(22) Filed: Sep. 26, 2008

(65) Prior Publication Data

US 2009/0076355 A1    Mar. 19, 2009

Related U.S. Application Data

(62) Division of application No. 11/145,048, filed on Jun. 3, 2005, now Pat. No. 7,620,437.

(51) Int. Cl.
*A61B 5/05* (2006.01)
*A61B 5/00* (2006.01)

(52) U.S. Cl. .................................. 600/347; 600/345

(58) Field of Classification Search .............. 600/309, 600/345–366
See application file for complete search history.

(56) References Cited

U.S. PATENT DOCUMENTS

| | | | |
|---|---|---|---|
| 2,508,253 A | 5/1950 | Haggardt |
| 2,915,579 A | 12/1959 | Mendelsohn |
| 3,374,337 A | 3/1968 | Burley |
| 3,510,747 A | 5/1970 | Petrides |
| 3,606,592 A | 9/1971 | Madurski et al. |
| 3,750,687 A | 8/1973 | Williams |
| 3,843,455 A | 10/1974 | Bier |
| 3,923,060 A | 12/1975 | Ellinwood |
| 3,930,493 A | 1/1976 | Williamson |
| 3,994,799 A | 11/1976 | Yao et al. |
| 4,018,547 A | 4/1977 | Rogen |
| 4,048,551 A | 9/1977 | Bosik |
| 4,121,282 A | 10/1978 | Ohsawa |
| 4,146,029 A | 3/1979 | Elinwood |
| 4,193,397 A | 3/1980 | Tucker et al. |
| 4,268,173 A | 5/1981 | Barnard et al. |
| 4,288,793 A | 9/1981 | Lotscher |
| 4,309,156 A | 1/1982 | Gonner et al. |
| 4,362,052 A | 12/1982 | Heath et al. |
| 4,401,122 A | 8/1983 | Clark, Jr. |
| 4,439,197 A | 3/1984 | Honda et al. |
| 4,447,224 A | 5/1984 | DeCant, Jr. et al. |
| 4,458,686 A | 7/1984 | Clark, Jr. |

(Continued)

FOREIGN PATENT DOCUMENTS

EP    0455455    11/1991

(Continued)

OTHER PUBLICATIONS

"An Electrochemical Slow Flow Meter", http://gore.ocean.washington.edu/research/slow_flow_meter.html, 2005, 3 pages.

(Continued)

*Primary Examiner* — Navin Natnithithadha (74) *Attorney, Agent, or Firm* — Jackson & Co., LLP (57) ABSTRACT

Method and apparatus for charging a power supply unit such as a rechargeable battery for use in data monitoring and management system using the ESD protection circuitry of the existing electrode contacts including guard contact and counter electrode thereby reducing system cost, complexity, and any unprotected battery contacts exposed for potential contamination is provided.

14 Claims, 5 Drawing Sheets

U.S. PATENT DOCUMENTS

| | | | |
|---|---|---|---|
| 4,467,811 A | 8/1984 | Clark, Jr. |
| 4,472,113 A | 9/1984 | Rogen |
| 4,474,309 A | 10/1984 | Solomon |
| 4,486,190 A | 12/1984 | Reinicke |
| 4,494,950 A | 1/1985 | Fischell |
| 4,512,348 A | 4/1985 | Uchigaki et al. |
| 4,524,343 A | 6/1985 | Morgan et al. |
| 4,529,401 A | 7/1985 | Leslie et al. |
| 4,531,235 A | 7/1985 | Brusen |
| 4,562,751 A | 1/1986 | Nason et al. |
| 4,563,249 A | 1/1986 | Hale |
| 4,570,492 A | 2/1986 | Walsh |
| 4,573,994 A | 3/1986 | Fischell et al. |
| 4,574,809 A | 3/1986 | Talish et al. |
| 4,633,878 A | 1/1987 | Bombardieri |
| 4,678,408 A | 7/1987 | Nason et al. |
| 4,685,903 A | 8/1987 | Cable et al. |
| 4,686,624 A | 8/1987 | Blum et al. |
| 4,736,748 A | 4/1988 | Nakamura et al. |
| 4,755,173 A | 7/1988 | Konopka et al. |
| 4,811,564 A | 3/1989 | Palmer |
| 4,850,959 A | 7/1989 | Findl |
| 4,851,827 A | 7/1989 | Nicholas |
| 4,866,396 A | 9/1989 | Tamura |
| 4,890,621 A | 1/1990 | Hakky |
| 4,953,552 A | 9/1990 | DeMarzo |
| 4,976,590 A | 12/1990 | Baldwin |
| 4,979,509 A | 12/1990 | Hakky |
| 4,984,581 A | 1/1991 | Stice |
| 5,004,532 A | 4/1991 | Hale et al. |
| 5,012,667 A | 5/1991 | Kruse |
| 5,019,974 A | 5/1991 | Beckers |
| 5,036,861 A | 8/1991 | Sembrowich et al. |
| 5,051,880 A | 9/1991 | Harm et al. |
| 5,061,914 A | 10/1991 | Busch et al. |
| 5,079,920 A | 1/1992 | Whitehead et al. |
| 5,081,421 A | 1/1992 | Miller et al. |
| 5,101,814 A | 4/1992 | Palti |
| 5,124,661 A | 6/1992 | Zelin et al. |
| 5,139,023 A | 8/1992 | Stanley et al. |
| 5,155,695 A | 10/1992 | Stein |
| 5,190,041 A | 3/1993 | Palti |
| 5,205,819 A | 4/1993 | Ross et al. |
| 5,207,666 A | 5/1993 | Idriss et al. |
| 5,211,371 A | 5/1993 | Coffee |
| 5,211,626 A | 5/1993 | Frank et al. |
| 5,223,822 A | 6/1993 | Stommes et al. |
| 5,262,305 A | 11/1993 | Heller et al. |
| 5,267,026 A | 11/1993 | Kawahara et al. |
| 5,278,997 A | 1/1994 | Martin |
| 5,284,423 A | 2/1994 | Holdsworth et al. |
| 5,291,614 A | 3/1994 | Baker et al. |
| 5,291,887 A | 3/1994 | Stanley et al. |
| 5,324,599 A | 6/1994 | Oyama et al. |
| 5,325,280 A | 6/1994 | Tortola et al. |
| 5,349,852 A | 9/1994 | Kamen et al. |
| 5,356,786 A | 10/1994 | Heller et al. |
| 5,366,292 A | 11/1994 | Voss |
| 5,368,028 A | 11/1994 | Palti |
| 5,371,687 A | 12/1994 | Holmes, II et al. |
| 5,372,133 A | 12/1994 | Hogen Esch |
| 5,376,070 A | 12/1994 | Purvis et al. |
| 5,382,331 A | 1/1995 | Banks |
| 5,390,671 A | 2/1995 | Lord et al. |
| 5,391,250 A | 2/1995 | Cheney, II et al. |
| 5,398,681 A | 3/1995 | Kuperschmidt |
| 5,404,585 A | 4/1995 | Vimpari et al. |
| 5,406,301 A | 4/1995 | Ravid |
| 5,445,611 A | 8/1995 | Eppstein et al. |
| 5,448,992 A | 9/1995 | Kuperschmidt |
| 5,458,140 A | 10/1995 | Eppstein et al. |
| 5,469,025 A | 11/1995 | Kanemori et al. |
| 5,479,486 A | 12/1995 | Saji |
| 5,494,562 A | 2/1996 | Maley et al. |
| 5,497,772 A | 3/1996 | Schulman et al. |
| 5,505,713 A | 4/1996 | Van Antwerp |
| 5,507,288 A | 4/1996 | Bocker et al. |
| 5,517,434 A | 5/1996 | Hanson et al. |
| 5,526,844 A | 6/1996 | Kamen et al. |
| 5,533,389 A | 7/1996 | Kamen et al. |
| 5,543,678 A | 8/1996 | Hoiberg |
| 5,559,528 A | 9/1996 | Ravid |
| 5,568,400 A | 10/1996 | Stark et al. |
| 5,568,806 A | 10/1996 | Cheney, II et al. |
| 5,575,770 A | 11/1996 | Melsky et al. |
| 5,576,535 A | 11/1996 | Oosterwijk et al. |
| 5,586,553 A | 12/1996 | Halili et al. |
| 5,593,852 A | 1/1997 | Heller et al. |
| 5,594,906 A | 1/1997 | Holmes, II et al. |
| 5,596,261 A | 1/1997 | Suyama |
| 5,601,435 A | 2/1997 | Quy |
| 5,604,404 A | 2/1997 | Sahara |
| 5,615,671 A | 4/1997 | Schoonen et al. |
| 5,622,413 A | 4/1997 | Kim et al. |
| 5,622,482 A | 4/1997 | Lee |
| 5,640,954 A | 6/1997 | Pfeiffer et al. |
| 5,645,709 A | 7/1997 | Birch et al. |
| 5,660,163 A | 8/1997 | Schulman et al. |
| 5,661,643 A | 8/1997 | Blakely et al. |
| 5,662,461 A | 9/1997 | Ono |
| 5,671,301 A | 9/1997 | Kuperschmidt |
| 5,685,844 A | 11/1997 | Marttila |
| 5,695,949 A | 12/1997 | Galen et al. |
| 5,703,928 A | 12/1997 | Galloway et al. |
| 5,707,502 A | 1/1998 | McCaffrey et al. |
| 5,708,247 A | 1/1998 | McAleer et al. |
| 5,711,861 A | 1/1998 | Ward et al. |
| 5,711,868 A | 1/1998 | Maley et al. |
| 5,722,397 A | 3/1998 | Eppstein |
| 5,741,211 A | 4/1998 | Renirie et al. |
| 5,748,872 A | 5/1998 | Norman |
| 5,759,510 A | 6/1998 | Pillai |
| 5,771,890 A | 6/1998 | Tamada |
| 5,774,254 A | 6/1998 | Berlin |
| 5,786,439 A | 7/1998 | Van Antwerp et al. |
| 5,790,297 A | 8/1998 | Berlin |
| 5,791,344 A | 8/1998 | Schulman et al. |
| 5,814,599 A | 9/1998 | Mitragotri et al. |
| 5,815,303 A | 9/1998 | Berlin |
| 5,822,715 A | 10/1998 | Worthington et al. |
| 5,825,488 A | 10/1998 | Kohl et al. |
| 5,848,990 A | 12/1998 | Cirelli et al. |
| 5,851,197 A | 12/1998 | Marano et al. |
| 5,856,631 A | 1/1999 | Julien |
| 5,873,026 A | 2/1999 | Reames |
| 5,875,417 A | 2/1999 | Golden |
| 5,885,211 A | 3/1999 | Eppstein et al. |
| 5,899,855 A | 5/1999 | Brown |
| 5,913,833 A | 6/1999 | Elstrom et al. |
| 5,918,603 A | 7/1999 | Brown |
| 5,919,167 A | 7/1999 | Mulhauser |
| 5,923,512 A | 7/1999 | Brownlow et al. |
| 5,947,921 A | 9/1999 | Johnson et al. |
| 5,948,512 A | 9/1999 | Kubota et al. |
| 5,951,582 A | 9/1999 | Thorne et al. |
| 5,951,836 A | 9/1999 | McAleer et al. |
| 5,954,643 A | 9/1999 | Van Antwerp et al. |
| 5,965,380 A | 10/1999 | Heller et al. |
| 5,968,011 A | 10/1999 | Larsen et al. |
| 5,971,922 A | 10/1999 | Arita et al. |
| 5,994,878 A | 11/1999 | Ostergaard et al. |
| 6,001,067 A | 12/1999 | Shults et al. |
| 6,002,961 A | 12/1999 | Mitragotri et al. |
| 6,011,486 A | 1/2000 | Casey |
| 6,014,577 A | 1/2000 | Henning et al. |
| 6,017,328 A | 1/2000 | Fischell et al. |
| 6,018,678 A | 1/2000 | Mitragotri et al. |
| 6,023,629 A | 2/2000 | Tamada |
| 6,024,539 A | 2/2000 | Blomquist et al. |
| 6,026,320 A | 2/2000 | Carlson et al. |
| 6,027,459 A | 2/2000 | Shain et al. |
| 6,027,496 A | 2/2000 | Loomis et al. |
| 6,027,692 A | 2/2000 | Galen et al. |
| 6,032,059 A | 2/2000 | Henning et al. |
| 6,041,253 A | 3/2000 | Kost et al. |
| 6,041,665 A | 3/2000 | Hussain |
| 6,059,546 A | 5/2000 | Brenan et al. |

| Patent No. | Kind | Date | Inventor |
|---|---|---|---|
| 6,063,039 | A | 5/2000 | Cunningham et al. |
| 6,064,368 | A | 5/2000 | Kang |
| 6,066,243 | A | 5/2000 | Anderson et al. |
| 6,067,017 | A | 5/2000 | Stewart et al. |
| 6,067,463 | A | 5/2000 | Jeng et al. |
| 6,071,249 | A | 6/2000 | Cunningham et al. |
| 6,071,251 | A | 6/2000 | Cunningham et al. |
| 6,073,031 | A | 6/2000 | Helstab et al. |
| 6,077,660 | A | 6/2000 | Wong et al. |
| 6,081,104 | A | 6/2000 | Kern |
| 6,083,710 | A | 7/2000 | Heller et al. |
| 6,085,871 | A | 7/2000 | Karamata |
| 6,086,575 | A | 7/2000 | Mejslov |
| 6,091,975 | A | 7/2000 | Daddona et al. |
| 6,093,156 | A | 7/2000 | Cunningham et al. |
| 6,093,172 | A | 7/2000 | Funderburk et al. |
| 6,121,009 | A | 9/2000 | Heller et al. |
| 6,129,823 | A | 10/2000 | Hughes et al. |
| 6,132,371 | A | 10/2000 | Dempsey et al. |
| 6,142,939 | A | 11/2000 | Eppstein et al. |
| 6,144,303 | A | 11/2000 | Federman |
| 6,144,869 | A | 11/2000 | Berner et al. |
| 6,144,922 | A | 11/2000 | Douglas et al. |
| 6,147,342 | A | 11/2000 | Kucher |
| 6,154,855 | A | 11/2000 | Norman |
| 6,155,992 | A | 12/2000 | Henning et al. |
| 6,157,442 | A | 12/2000 | Raskas |
| 6,160,449 | A | 12/2000 | Klomsdorf et al. |
| 6,162,202 | A | 12/2000 | Sicurelli et al. |
| 6,162,611 | A | 12/2000 | Heller et al. |
| 6,164,284 | A | 12/2000 | Schulman et al. |
| 6,173,160 | B1 | 1/2001 | Liimatainen |
| 6,175,752 | B1 | 1/2001 | Say et al. |
| 6,180,416 | B1 | 1/2001 | Kurnik et al. |
| 6,185,452 | B1 | 2/2001 | Schulman et al. |
| 6,201,980 | B1 | 3/2001 | Darrow et al. |
| 6,206,841 | B1 | 3/2001 | Cunningham et al. |
| 6,208,894 | B1 | 3/2001 | Schulman et al. |
| 6,212,416 | B1 | 4/2001 | Ward et al. |
| 6,215,206 | B1 | 4/2001 | Chitayat |
| 6,222,514 | B1 | 4/2001 | DeLuca |
| 6,228,100 | B1 | 5/2001 | Schraga |
| 6,232,370 | B1 | 5/2001 | Kubota et al. |
| 6,233,471 | B1 | 5/2001 | Berner et al. |
| 6,233,539 | B1 | 5/2001 | Brown |
| 6,242,961 | B1 | 6/2001 | Liu et al. |
| 6,245,060 | B1 | 6/2001 | Loomis et al. |
| 6,248,067 | B1 | 6/2001 | Causey, III et al. |
| 6,262,708 | B1 | 7/2001 | Chu |
| 6,272,364 | B1 | 8/2001 | Kurnik |
| 6,278,425 | B1 | 8/2001 | DeLuca |
| 6,280,587 | B1 | 8/2001 | Matsumoto |
| 6,283,926 | B1 | 9/2001 | Cunningham et al. |
| 6,284,478 | B1 | 9/2001 | Heller et al. |
| 6,288,653 | B1 | 9/2001 | Shih |
| 6,293,925 | B1 | 9/2001 | Safabash et al. |
| 6,295,506 | B1 | 9/2001 | Heinonen et al. |
| 6,298,254 | B2 | 10/2001 | Tamada |
| 6,298,255 | B1 | 10/2001 | Cordero et al. |
| 6,299,578 | B1 | 10/2001 | Kurnik et al. |
| 6,301,499 | B1 | 10/2001 | Carlson et al. |
| 6,306,104 | B1 | 10/2001 | Cunningham et al. |
| 6,309,351 | B1 | 10/2001 | Kurnik et al. |
| 6,312,888 | B1 | 11/2001 | Wong et al. |
| 6,315,721 | B2 | 11/2001 | Schulman et al. |
| 6,326,160 | B1 | 12/2001 | Dunn et al. |
| 6,329,161 | B1 | 12/2001 | Heller et al. |
| 6,341,232 | B1 | 1/2002 | Conn et al. |
| 6,356,776 | B1 | 3/2002 | Berner et al. |
| 6,360,888 | B1 | 3/2002 | McIvor et al. |
| 6,366,793 | B1 | 4/2002 | Bell et al. |
| 6,368,141 | B1 | 4/2002 | Van Antwerp et al. |
| 6,368,274 | B1 | 4/2002 | Van Antwerp et al. |
| 6,372,371 | B1 | 4/2002 | Iarochenko et al. |
| 6,375,344 | B1 | 4/2002 | Hanson et al. |
| 6,375,638 | B2 | 4/2002 | Nason et al. |
| 6,377,894 | B1 | 4/2002 | Deweese et al. |
| 6,379,301 | B1 | 4/2002 | Worthington et al. |
| 6,381,496 | B1 | 4/2002 | Meadows et al. |
| 6,393,318 | B1 | 5/2002 | Conn et al. |
| 6,403,944 | B1 | 6/2002 | MacKenzie et al. |
| 6,405,066 | B1 | 6/2002 | Essenpreis et al. |
| 6,408,402 | B1 | 6/2002 | Norman |
| 6,417,074 | B2 | 7/2002 | Kopley et al. |
| 6,419,642 | B1 | 7/2002 | Marchitto et al. |
| 6,425,829 | B1 | 7/2002 | Julien |
| 6,427,088 | B1 | 7/2002 | Bowman, IV et al. |
| 6,432,585 | B1 | 8/2002 | Kawakami et al. |
| 6,437,379 | B2 | 8/2002 | Kopley et al. |
| 6,438,385 | B1 | 8/2002 | Heinonen et al. |
| 6,438,414 | B1 | 8/2002 | Conn et al. |
| 6,442,413 | B1 | 8/2002 | Silver |
| 6,461,329 | B1 | 10/2002 | Van Antwerp et al. |
| 6,462,162 | B2 | 10/2002 | Van Antwerp et al. |
| 6,464,848 | B1 | 10/2002 | Matsumoto |
| 6,466,807 | B1 | 10/2002 | Dobson et al. |
| 6,466,810 | B1 | 10/2002 | Ward et al. |
| 6,468,222 | B1 | 10/2002 | Mault et al. |
| 6,471,980 | B2 | 10/2002 | Sirhan et al. |
| 6,472,991 | B1 | 10/2002 | Schulman et al. |
| 6,475,196 | B1 | 11/2002 | Vachon |
| 6,478,736 | B1 | 11/2002 | Mault |
| 6,480,730 | B2 | 11/2002 | Darrow et al. |
| 6,482,158 | B2 | 11/2002 | Mault |
| 6,484,045 | B1 | 11/2002 | Holker et al. |
| 6,485,138 | B1 | 11/2002 | Kubota et al. |
| 6,485,461 | B1 | 11/2002 | Mason et al. |
| 6,485,465 | B2 | 11/2002 | Morberg et al. |
| 6,492,180 | B2 | 12/2002 | Brown et al. |
| 6,506,168 | B1 | 1/2003 | Fathallah et al. |
| 6,513,532 | B2 | 2/2003 | Mault et al. |
| 6,514,460 | B1 | 2/2003 | Fendrock |
| 6,514,689 | B2 | 2/2003 | Han et al. |
| 6,514,718 | B2 | 2/2003 | Heller et al. |
| 6,522,530 | B2 | 2/2003 | Bang |
| 6,525,330 | B2 | 2/2003 | Paolini et al. |
| 6,526,298 | B1 | 2/2003 | Khalil et al. |
| 6,529,772 | B2 | 3/2003 | Carlson et al. |
| 6,530,915 | B1 | 3/2003 | Eppstein et al. |
| 6,535,753 | B1 | 3/2003 | Raskas |
| 6,537,243 | B1 | 3/2003 | Henning et al. |
| 6,540,675 | B2 | 4/2003 | Aceti et al. |
| 6,540,891 | B1 | 4/2003 | Stewart et al. |
| 6,543,224 | B1 | 4/2003 | Barooah |
| 6,544,212 | B2 | 4/2003 | Galley et al. |
| 6,546,269 | B1 | 4/2003 | Kurnik |
| 6,549,796 | B2 | 4/2003 | Sohrab |
| 6,551,276 | B1 | 4/2003 | Mann et al. |
| 6,554,798 | B1 | 4/2003 | Mann et al. |
| 6,558,320 | B1 | 5/2003 | Causey, III et al. |
| 6,558,321 | B1 | 5/2003 | Burd et al. |
| 6,558,351 | B1 | 5/2003 | Steil et al. |
| 6,560,471 | B1 | 5/2003 | Heller et al. |
| 6,561,978 | B1 | 5/2003 | Conn et al. |
| 6,562,001 | B2 | 5/2003 | Lebel et al. |
| 6,564,105 | B2 | 5/2003 | Starkweather et al. |
| 6,564,807 | B1 | 5/2003 | Schulman et al. |
| 6,565,509 | B1 | 5/2003 | Say et al. |
| 6,565,738 | B1 | 5/2003 | Henning et al. |
| 6,569,157 | B1 | 5/2003 | Shain et al. |
| 6,571,128 | B2 | 5/2003 | Lebel et al. |
| 6,571,200 | B1 | 5/2003 | Mault |
| 6,576,117 | B1 | 6/2003 | Iketaki et al. |
| 6,577,899 | B2 | 6/2003 | Lebel et al. |
| 6,579,498 | B1 | 6/2003 | Eglise |
| 6,579,690 | B1 | 6/2003 | Bonnacaze et al. |
| 6,582,393 | B2 | 6/2003 | Sage, Jr. |
| 6,585,644 | B2 | 7/2003 | Lebel et al. |
| 6,586,971 | B1 | 7/2003 | Naffziger et al. |
| 6,587,705 | B1 | 7/2003 | Kim et al. |
| 6,589,229 | B1 | 7/2003 | Connelly et al. |
| 6,594,514 | B2 | 7/2003 | Berner et al. |
| 6,595,919 | B2 | 7/2003 | Berner et al. |
| 6,596,016 | B1 | 7/2003 | Vreman et al. |
| 6,600,997 | B2 | 7/2003 | Deweese et al. |
| 6,602,469 | B1 | 8/2003 | Maus et al. |
| 6,607,509 | B2 | 8/2003 | Bobroff et al. |
| 6,610,012 | B2 | 8/2003 | Mault |

| Patent | | Date | Inventor |
|---|---|---|---|
| 6,612,306 | B1 | 9/2003 | Mault |
| 6,615,061 | B1 | 9/2003 | Khalil et al. |
| 6,615,074 | B2 | 9/2003 | Mickle et al. |
| 6,618,603 | B2 | 9/2003 | Varalli et al. |
| 6,620,106 | B2 | 9/2003 | Mault |
| 6,623,501 | B2 | 9/2003 | Heller et al. |
| 6,629,934 | B2 | 10/2003 | Mault et al. |
| 6,633,095 | B1 | 10/2003 | Swope et al. |
| 6,633,772 | B2 | 10/2003 | Ford et al. |
| 6,635,014 | B2 | 10/2003 | Starkweather et al. |
| 6,641,533 | B2 | 11/2003 | Causey, III et al. |
| 6,645,142 | B2 | 11/2003 | Braig et al. |
| 6,648,821 | B2 | 11/2003 | Lebel et al. |
| 6,650,064 | B2 | 11/2003 | Guthrie et al. |
| 6,653,091 | B1 | 11/2003 | Dunn et al. |
| 6,656,158 | B2 | 12/2003 | Mahoney et al. |
| 6,656,159 | B2 | 12/2003 | Flaherty |
| 6,659,948 | B2 | 12/2003 | Lebel et al. |
| 6,659,980 | B2 | 12/2003 | Morberg et al. |
| 6,668,196 | B1 | 12/2003 | Villegas et al. |
| 6,669,663 | B1 | 12/2003 | Thompson |
| 6,669,669 | B2 | 12/2003 | Flaherty et al. |
| 6,670,806 | B2 | 12/2003 | Wendt et al. |
| 6,679,841 | B2 | 1/2004 | Bojan et al. |
| 6,687,522 | B2 | 2/2004 | Tamada |
| 6,687,546 | B2 | 2/2004 | Lebel et al. |
| 6,692,457 | B2 | 2/2004 | Flaherty |
| 6,694,191 | B2 | 2/2004 | Starkweather et al. |
| 6,695,885 | B2 | 2/2004 | Schulman et al. |
| 6,699,218 | B2 | 3/2004 | Flaherty et al. |
| 6,702,857 | B2 | 3/2004 | Brauker et al. |
| 6,723,072 | B2 | 4/2004 | Flaherty et al. |
| 6,728,560 | B2 | 4/2004 | Kollias et al. |
| 6,730,200 | B1 | 5/2004 | Stewart et al. |
| 6,731,976 | B2 | 5/2004 | Penn et al. |
| 6,733,446 | B2 | 5/2004 | Lebel et al. |
| 6,736,777 | B2 | 5/2004 | Kim et al. |
| 6,736,797 | B1 | 5/2004 | Larsen et al. |
| 6,738,654 | B2 | 5/2004 | Sohrab |
| 6,740,059 | B2 | 5/2004 | Flaherty |
| 6,740,075 | B2 | 5/2004 | Lebel et al. |
| 6,741,877 | B1 | 5/2004 | Shults et al. |
| 6,743,635 | B2 | 6/2004 | Neel et al. |
| 6,749,587 | B2 | 6/2004 | Flaherty |
| 6,752,785 | B2 | 6/2004 | Van Antwerp et al. |
| 6,752,787 | B1 | 6/2004 | Causey, III et al. |
| 6,758,810 | B2 | 7/2004 | Lebel et al. |
| 6,764,581 | B1 | 7/2004 | Forrow et al. |
| 6,768,425 | B2 | 7/2004 | Flaherty et al. |
| 6,770,030 | B1 | 8/2004 | Schaupp et al. |
| 6,770,729 | B2 | 8/2004 | Van Antwerp |
| 6,773,563 | B2 | 8/2004 | Matsumoto |
| 6,779,984 | B2 | 8/2004 | Lilie et al. |
| 6,790,178 | B1 | 9/2004 | Mault et al. |
| 6,794,195 | B2 | 9/2004 | Colvin, Jr. |
| 6,799,861 | B2 | 10/2004 | Naghi et al. |
| 6,809,653 | B1 | 10/2004 | Mann et al. |
| 6,810,290 | B2 | 10/2004 | Lebel et al. |
| 6,811,533 | B2 | 11/2004 | Lebel et al. |
| 6,811,534 | B2 | 11/2004 | Bowman, IV et al. |
| 6,813,519 | B2 | 11/2004 | Lebel et al. |
| 6,816,742 | B2 | 11/2004 | Kim et al. |
| 6,818,348 | B1 | 11/2004 | Venkatesan et al. |
| 6,830,558 | B2 | 12/2004 | Flaherty et al. |
| 6,832,114 | B1 | 12/2004 | Whitehurst et al. |
| 6,833,540 | B2 | 12/2004 | MacKenzie et al. |
| 6,835,553 | B2 | 12/2004 | Han et al. |
| 6,837,858 | B2 | 1/2005 | Cunningham et al. |
| 6,839,596 | B2 | 1/2005 | Nelson et al. |
| 6,840,912 | B2 | 1/2005 | Kloepfer et al. |
| 6,849,237 | B2 | 2/2005 | Housefield et al. |
| 6,850,790 | B2 | 2/2005 | Berner et al. |
| 6,859,831 | B1 | 2/2005 | Gelvin et al. |
| 6,862,465 | B2 | 3/2005 | Shults et al. |
| 6,872,200 | B2 | 3/2005 | Mann et al. |
| 6,873,268 | B2 | 3/2005 | Lebel et al. |
| 6,881,551 | B2 | 4/2005 | Heller et al. |
| 6,892,085 | B2 | 5/2005 | McIvor et al. |
| 6,893,396 | B2 | 5/2005 | Schulze et al. |
| 6,895,265 | B2 | 5/2005 | Silver |
| 6,898,451 | B2 | 5/2005 | Wuori |
| 6,899,683 | B2 | 5/2005 | Mault et al. |
| 6,899,684 | B2 | 5/2005 | Mault et al. |
| 6,904,301 | B2 | 6/2005 | Raskas |
| 6,907,127 | B1 | 6/2005 | Kravitz et al. |
| 6,908,535 | B2 | 6/2005 | Rankin et al. |
| 6,916,159 | B2 | 7/2005 | Rush et al. |
| 6,918,874 | B1 | 7/2005 | Hatch et al. |
| 6,922,576 | B2 | 7/2005 | Raskas |
| 6,922,578 | B2 | 7/2005 | Eppstein et al. |
| 6,923,764 | B2 | 8/2005 | Aceti et al. |
| 6,931,327 | B2 | 8/2005 | Goode, Jr. et al. |
| 6,936,029 | B2 | 8/2005 | Mann et al. |
| 6,949,816 | B2 | 9/2005 | Brown et al. |
| 6,950,708 | B2 | 9/2005 | Bowman, IV et al. |
| 6,952,603 | B2 | 10/2005 | Gerber et al. |
| 6,955,650 | B2 | 10/2005 | Mault et al. |
| 6,958,129 | B2 | 10/2005 | Galen et al. |
| 6,958,705 | B2 | 10/2005 | Lebel et al. |
| 6,960,192 | B1 | 11/2005 | Flaherty et al. |
| 6,961,448 | B2 | 11/2005 | Nichols et al. |
| 6,974,437 | B2 | 12/2005 | Lebel et al. |
| 6,979,326 | B2 | 12/2005 | Mann et al. |
| 6,990,366 | B2 | 1/2006 | Say et al. |
| 6,990,372 | B2 | 1/2006 | Perron et al. |
| 6,997,911 | B2 | 2/2006 | Klitmose |
| 6,997,920 | B2 | 2/2006 | Mann et al. |
| 6,999,810 | B2 | 2/2006 | Berner et al. |
| 7,003,340 | B2 | 2/2006 | Say et al. |
| 7,003,341 | B2 | 2/2006 | Say et al. |
| 7,005,857 | B2 | 2/2006 | Stiene et al. |
| 7,006,858 | B2 | 2/2006 | Silver et al. |
| 7,010,356 | B2 | 3/2006 | Jog et al. |
| 7,011,630 | B2 | 3/2006 | Desai et al. |
| 7,018,360 | B2 | 3/2006 | Flaherty et al. |
| 7,020,508 | B2 | 3/2006 | Stirovic et al. |
| 7,024,245 | B2 | 4/2006 | Lebel et al. |
| 7,024,249 | B2 | 4/2006 | Weisner et al. |
| 7,025,743 | B2 | 4/2006 | Mann et al. |
| 7,029,444 | B2 | 4/2006 | Shin et al. |
| 7,029,455 | B2 | 4/2006 | Flaherty |
| 7,034,677 | B2 | 4/2006 | Steinthal et al. |
| 7,041,468 | B2 | 5/2006 | Drucker et al. |
| 7,043,287 | B1 | 5/2006 | Khalil et al. |
| 7,052,251 | B2 | 5/2006 | Nason et al. |
| 7,067,498 | B2 | 6/2006 | Wolf et al. |
| 7,070,591 | B2 | 7/2006 | Adams et al. |
| 7,072,738 | B2 | 7/2006 | Bonney et al. |
| 7,074,307 | B2 | 7/2006 | Simpson et al. |
| 7,077,328 | B2 | 7/2006 | Krishnaswamy et al. |
| 7,079,901 | B1 | 7/2006 | Loftin et al. |
| 7,081,195 | B2 | 7/2006 | Simpson et al. |
| 7,083,593 | B2 | 8/2006 | Stultz |
| 7,086,277 | B2 | 8/2006 | Tess et al. |
| 7,092,762 | B1 | 8/2006 | Loftin et al. |
| 7,097,983 | B2 | 8/2006 | Markovsky et al. |
| 7,098,803 | B2 | 8/2006 | Mann et al. |
| 7,108,711 | B2 | 9/2006 | Vogel et al. |
| 7,108,778 | B2 | 9/2006 | Simpson et al. |
| 7,110,803 | B2 | 9/2006 | Shults et al. |
| 7,114,502 | B2 | 10/2006 | Schulman et al. |
| 7,123,206 | B2 | 10/2006 | Hess et al. |
| 7,133,710 | B2 | 11/2006 | Acosta et al. |
| 7,134,999 | B2 | 11/2006 | Brauker et al. |
| 7,136,689 | B2 | 11/2006 | Shults et al. |
| 7,136,704 | B2 | 11/2006 | Schulman |
| 7,137,964 | B2 | 11/2006 | Flaherty |
| 7,144,384 | B2 | 12/2006 | Gorman et al. |
| 7,149,581 | B2 | 12/2006 | Goedeke |
| 7,153,212 | B1 | 12/2006 | Karten et al. |
| 7,154,398 | B2 | 12/2006 | Chen et al. |
| 7,163,511 | B2 | 1/2007 | Conn et al. |
| 7,167,818 | B2 | 1/2007 | Brown |
| 7,171,274 | B2 | 1/2007 | Starkweather et al. |
| 7,181,261 | B2 | 2/2007 | Silver et al. |
| 7,186,566 | B2 | 3/2007 | Qian |
| 7,186,791 | B2 | 3/2007 | Bruno et al. |
| 7,192,450 | B2 | 3/2007 | Brauker et al. |

| | | |
|---|---|---|
| 7,193,521 B2 | 3/2007 | Morberg et al. |
| 7,198,603 B2 | 4/2007 | Penner et al. |
| 7,202,734 B1 | 4/2007 | Raab |
| 7,205,409 B2 | 4/2007 | Pei et al. |
| 7,208,119 B1 | 4/2007 | Kurtock et al. |
| 7,211,048 B1 | 5/2007 | Najafi et al. |
| 7,218,017 B1 | 5/2007 | Chitayet et al. |
| 7,225,535 B2 | 6/2007 | Feldman et al. |
| 7,226,278 B2 | 6/2007 | Nason et al. |
| 7,226,442 B2 | 6/2007 | Sheppard, Jr. et al. |
| 7,226,978 B2 | 6/2007 | Tapsak et al. |
| 7,258,666 B2 | 8/2007 | Brown |
| 7,266,400 B2 | 9/2007 | Fine et al. |
| 7,276,029 B2 | 10/2007 | Goode, Jr. et al. |
| 7,283,867 B2 | 10/2007 | Strother et al. |
| 7,299,080 B2 | 11/2007 | Acosta et al. |
| 7,303,549 B2 | 12/2007 | Flaherty et al. |
| 7,310,544 B2 | 12/2007 | Brister et al. |
| 7,323,091 B1 | 1/2008 | Gillette et al. |
| 7,324,949 B2 | 1/2008 | Bristol |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,424,318 B2 | 9/2008 | Brister et al. |
| 7,436,511 B2 | 10/2008 | Ruchti et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,480,138 B2 | 1/2009 | Kogan et al. |
| 7,494,465 B2 | 2/2009 | Brister et al. |
| 7,497,827 B2 | 3/2009 | Brister et al. |
| 7,510,526 B2 | 3/2009 | Merry et al. |
| 7,519,408 B2 | 4/2009 | Rasdal et al. |
| 7,583,190 B2 | 9/2009 | Reggiardo et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,613,491 B2 | 11/2009 | Boock et al. |
| 7,615,007 B2 | 11/2009 | Shults et al. |
| 7,620,437 B2 | 11/2009 | Reggiardo |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,679,407 B2 | 3/2010 | Reggiardo |
| 7,711,402 B2 | 5/2010 | Shults et al. |
| 7,713,574 B2 | 5/2010 | Brister et al. |
| 7,715,893 B2 | 5/2010 | Kamath et al. |
| 7,727,181 B2 | 6/2010 | Rush et al. |
| 7,753,873 B2 | 7/2010 | Rush |
| 7,753,874 B2 | 7/2010 | Rush et al. |
| 7,756,561 B2 | 7/2010 | Reggiardo et al. |
| 7,766,864 B2 | 8/2010 | Rush et al. |
| 2001/0016682 A1 | 8/2001 | Berner et al. |
| 2001/0016683 A1 | 8/2001 | Darrow et al. |
| 2001/0016710 A1 | 8/2001 | Nason et al. |
| 2001/0020124 A1 | 9/2001 | Tamada |
| 2001/0023095 A1 | 9/2001 | Kopley et al. |
| 2001/0024864 A1 | 9/2001 | Kopley et al. |
| 2001/0029340 A1 | 10/2001 | Mault et al. |
| 2001/0034502 A1 | 10/2001 | Moberg et al. |
| 2001/0037060 A1 | 11/2001 | Thompson et al. |
| 2001/0037069 A1 | 11/2001 | Carlson et al. |
| 2001/0041830 A1 | 11/2001 | Varalli et al. |
| 2001/0044581 A1 | 11/2001 | Mault |
| 2001/0044588 A1 | 11/2001 | Mault |
| 2001/0049470 A1 | 12/2001 | Mault et al. |
| 2001/0053891 A1 | 12/2001 | Ackley |
| 2001/0056255 A1 | 12/2001 | Kost et al. |
| 2002/0002326 A1 | 1/2002 | Causey, III et al. |
| 2002/0002328 A1 | 1/2002 | Tamada |
| 2002/0004640 A1 | 1/2002 | Conn et al. |
| 2002/0010414 A1 | 1/2002 | Coston et al. |
| 2002/0019022 A1 | 2/2002 | Dunn et al. |
| 2002/0026937 A1 | 3/2002 | Mault |
| 2002/0027164 A1 | 3/2002 | Mault et al. |
| 2002/0028995 A1 | 3/2002 | Mault |
| 2002/0032374 A1 | 3/2002 | Holker et al. |
| 2002/0040208 A1 | 4/2002 | Flaherty et al. |
| 2002/0042090 A1 | 4/2002 | Heller et al. |
| 2002/0047867 A1 | 4/2002 | Mault et al. |
| 2002/0053637 A1 | 5/2002 | Conn et al. |
| 2002/0062069 A1 | 5/2002 | Mault |
| 2002/0068858 A1 | 6/2002 | Braig et al. |
| 2002/0077765 A1 | 6/2002 | Mault |
| 2002/0077766 A1 | 6/2002 | Mault |
| 2002/0087056 A1 | 7/2002 | Aceti et al. |
| 2002/0091312 A1 | 7/2002 | Berner et al. |
| 2002/0091454 A1 | 7/2002 | Vasko |
| 2002/0103425 A1 | 8/2002 | Mault |
| 2002/0107433 A1 | 8/2002 | Mault |
| 2002/0107476 A1 | 8/2002 | Mann et al. |
| 2002/0109600 A1 | 8/2002 | Mault et al. |
| 2002/0118090 A1 | 8/2002 | Park et al. |
| 2002/0119711 A1 | 8/2002 | Van Antwerp et al. |
| 2002/0124017 A1 | 9/2002 | Mault |
| 2002/0133378 A1 | 9/2002 | Mault et al. |
| 2002/0161286 A1 | 10/2002 | Gerber et al. |
| 2002/0169394 A1 | 11/2002 | Eppstein et al. |
| 2002/0177764 A1 | 11/2002 | Sohrab |
| 2002/0193679 A1 | 12/2002 | Malave et al. |
| 2003/0009133 A1 | 1/2003 | Ramey |
| 2003/0023182 A1 | 1/2003 | Mault et al. |
| 2003/0023317 A1 | 1/2003 | Brauker et al. |
| 2003/0028089 A1 | 2/2003 | Galley et al. |
| 2003/0028120 A1 | 2/2003 | Mault et al. |
| 2003/0032868 A1 | 2/2003 | Graskov et al. |
| 2003/0032874 A1 | 2/2003 | Rhodes et al. |
| 2003/0040683 A1 | 2/2003 | Rule et al. |
| 2003/0050546 A1 | 3/2003 | Desai et al. |
| 2003/0050575 A1 | 3/2003 | Diermann et al. |
| 2003/0060692 A1 | 3/2003 | Ruchti et al. |
| 2003/0060765 A1 | 3/2003 | Campbell et al. |
| 2003/0065257 A1 | 4/2003 | Mault et al. |
| 2003/0065273 A1 | 4/2003 | Mault et al. |
| 2003/0065274 A1 | 4/2003 | Mault et al. |
| 2003/0065275 A1 | 4/2003 | Mault et al. |
| 2003/0065308 A1 | 4/2003 | Lebel et al. |
| 2003/0078560 A1 | 4/2003 | Miller et al. |
| 2003/0100040 A1 | 5/2003 | Bonnecaze et al. |
| 2003/0100821 A1 | 5/2003 | Heller et al. |
| 2003/0105407 A1 | 6/2003 | Pearce, Jr. et al. |
| 2003/0107487 A1 | 6/2003 | Korman et al. |
| 2003/0108976 A1 | 6/2003 | Braig et al. |
| 2003/0118460 A1 | 6/2003 | Lilie et al. |
| 2003/0130616 A1 | 7/2003 | Steil et al. |
| 2003/0134347 A1 | 7/2003 | Heller et al. |
| 2003/0135100 A1 | 7/2003 | Kim et al. |
| 2003/0135333 A1 | 7/2003 | Aceti et al. |
| 2003/0153820 A1 | 8/2003 | Berner et al. |
| 2003/0153821 A1 | 8/2003 | Berner et al. |
| 2003/0158472 A1 | 8/2003 | Sohrab |
| 2003/0158707 A1 | 8/2003 | Doi |
| 2003/0175806 A1 | 9/2003 | Rule et al. |
| 2003/0176933 A1 | 9/2003 | Lebel et al. |
| 2003/0181851 A1 | 9/2003 | Mann et al. |
| 2003/0181852 A1 | 9/2003 | Mann et al. |
| 2003/0187338 A1 | 10/2003 | Say et al. |
| 2003/0187525 A1 | 10/2003 | Mann et al. |
| 2003/0191376 A1 | 10/2003 | Samuels et al. |
| 2003/0191431 A1 | 10/2003 | Mann et al. |
| 2003/0195403 A1 | 10/2003 | Berner et al. |
| 2003/0195462 A1 | 10/2003 | Mann et al. |
| 2003/0198558 A1 | 10/2003 | Nason et al. |
| 2003/0199825 A1 | 10/2003 | Flaherty |
| 2003/0199837 A1 | 10/2003 | Vachon |
| 2003/0208110 A1 | 11/2003 | Mault et al. |
| 2003/0208113 A1 | 11/2003 | Mault et al. |
| 2003/0208133 A1 | 11/2003 | Mault |
| 2003/0208154 A1 | 11/2003 | Close et al. |
| 2003/0208409 A1 | 11/2003 | Mault |
| 2003/0212346 A1 | 11/2003 | Yuzhakov et al. |
| 2003/0212364 A1 | 11/2003 | Mann et al. |
| 2003/0212379 A1 | 11/2003 | Bylund et al. |
| 2003/0217966 A1 | 11/2003 | Tapsak et al. |

| | | |
|---|---|---|
| 2003/0225360 A1 | 12/2003 | Eppstein et al. |
| 2003/0225361 A1 | 12/2003 | Sabra |
| 2003/0226695 A1 | 12/2003 | Mault |
| 2003/0232370 A1 | 12/2003 | Trifiro |
| 2003/0235817 A1 | 12/2003 | Bartkowiak et al. |
| 2004/0011671 A1 | 1/2004 | Shults et al. |
| 2004/0018486 A1 | 1/2004 | Dunn et al. |
| 2004/0019321 A1 | 1/2004 | Sage et al. |
| 2004/0027253 A1 | 2/2004 | Marsh et al. |
| 2004/0030226 A1 | 2/2004 | Quy |
| 2004/0039256 A1 | 2/2004 | Kawatahara et al. |
| 2004/0045879 A1 | 3/2004 | Shults et al. |
| 2004/0054263 A1 | 3/2004 | Moerman et al. |
| 2004/0059201 A1 | 3/2004 | Ginsberg |
| 2004/0064133 A1 | 4/2004 | Miller et al. |
| 2004/0072357 A1 | 4/2004 | Stiene et al. |
| 2004/0073095 A1 | 4/2004 | Causey, III et al. |
| 2004/0085215 A1 | 5/2004 | Moberg et al. |
| 2004/0096959 A1 | 5/2004 | Stiene et al. |
| 2004/0100376 A1 | 5/2004 | Lye et al. |
| 2004/0106858 A1 | 6/2004 | Say et al. |
| 2004/0106859 A1 | 6/2004 | Say et al. |
| 2004/0106860 A1 | 6/2004 | Say et al. |
| 2004/0108226 A1 | 6/2004 | Polychronakos et al. |
| 2004/0115067 A1 | 6/2004 | Rush et al. |
| 2004/0122353 A1 | 6/2004 | Shahmirian et al. |
| 2004/0132220 A1 | 7/2004 | Fish |
| 2004/0133092 A1 | 7/2004 | Kain |
| 2004/0152622 A1 | 8/2004 | Keith et al. |
| 2004/0158137 A1 | 8/2004 | Eppstein et al. |
| 2004/0162473 A1 | 8/2004 | Sohrab |
| 2004/0164961 A1 | 8/2004 | Bal et al. |
| 2004/0167383 A1 | 8/2004 | Kim et al. |
| 2004/0167801 A1 | 8/2004 | Say et al. |
| 2004/0171921 A1 | 9/2004 | Say et al. |
| 2004/0176913 A1 | 9/2004 | Kawatahara et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0199059 A1 | 10/2004 | Brauker et al. |
| 2004/0202576 A1 | 10/2004 | Aceti et al. |
| 2004/0207054 A1 | 10/2004 | Brown et al. |
| 2004/0208780 A1 | 10/2004 | Faries, Jr. et al. |
| 2004/0210184 A1 | 10/2004 | Kost et al. |
| 2004/0225338 A1 | 11/2004 | Lebel et al. |
| 2004/0236200 A1 | 11/2004 | Say et al. |
| 2004/0248204 A1 | 12/2004 | Moerman |
| 2004/0249250 A1 | 12/2004 | McGee et al. |
| 2004/0249253 A1 | 12/2004 | Racchini et al. |
| 2004/0249254 A1 | 12/2004 | Racchini et al. |
| 2004/0249999 A1 | 12/2004 | Connolly et al. |
| 2004/0253736 A1 | 12/2004 | Stout et al. |
| 2004/0254429 A1 | 12/2004 | Yang |
| 2004/0254434 A1 | 12/2004 | Goodnow et al. |
| 2004/0263354 A1 | 12/2004 | Mann et al. |
| 2004/0264396 A1 | 12/2004 | Ginzburg et al. |
| 2005/0003470 A1 | 1/2005 | Nelson et al. |
| 2005/0009126 A1 | 1/2005 | Andrews et al. |
| 2005/0010269 A1 | 1/2005 | Lebel et al. |
| 2005/0016276 A1 | 1/2005 | Guan et al. |
| 2005/0027179 A1 | 2/2005 | Berner et al. |
| 2005/0027180 A1 | 2/2005 | Goode, Jr. et al. |
| 2005/0027181 A1 | 2/2005 | Goode, Jr. et al. |
| 2005/0027462 A1 | 2/2005 | Goode, Jr. et al. |
| 2005/0027463 A1 | 2/2005 | Goode, Jr. et al. |
| 2005/0031689 A1 | 2/2005 | Shults et al. |
| 2005/0033132 A1 | 2/2005 | Shults et al. |
| 2005/0038680 A1 | 2/2005 | McMahon |
| 2005/0043598 A1 | 2/2005 | Goode, Jr. et al. |
| 2005/0043894 A1 | 2/2005 | Fernandez |
| 2005/0045476 A1 | 3/2005 | Neel et al. |
| 2005/0049473 A1 | 3/2005 | Desai et al. |
| 2005/0051580 A1 | 3/2005 | Ramey |
| 2005/0053365 A1 | 3/2005 | Adams et al. |
| 2005/0054909 A1 | 3/2005 | Petisce et al. |
| 2005/0059926 A1 | 3/2005 | Sage, Jr. et al. |
| 2005/0065464 A1 | 3/2005 | Talbot et al. |
| 2005/0090607 A1 | 4/2005 | Tapsak et al. |
| 2005/0090808 A1 | 4/2005 | Malave et al. |
| 2005/0112169 A1 | 5/2005 | Brauker et al. |
| 2005/0113657 A1 | 5/2005 | Alarcon et al. |
| 2005/0113658 A1 | 5/2005 | Jacobson et al. |
| 2005/0118726 A1 | 6/2005 | Schultz et al. |
| 2005/0121322 A1 | 6/2005 | Say et al. |
| 2005/0124873 A1 | 6/2005 | Shults et al. |
| 2005/0137471 A1 | 6/2005 | Haar et al. |
| 2005/0143635 A1 | 6/2005 | Kamath et al. |
| 2005/0143636 A1 | 6/2005 | Zhang et al. |
| 2005/0148003 A1 | 7/2005 | Keith et al. |
| 2005/0154271 A1 | 7/2005 | Rasdal et al. |
| 2005/0161346 A1 | 7/2005 | Simpson et al. |
| 2005/0171503 A1 | 8/2005 | Van Den Berghe et al. |
| 2005/0171512 A1 | 8/2005 | Flaherty |
| 2005/0171513 A1 | 8/2005 | Mann et al. |
| 2005/0173245 A1 | 8/2005 | Feldman et al. |
| 2005/0176136 A1 | 8/2005 | Burd et al. |
| 2005/0177036 A1 | 8/2005 | Shults et al. |
| 2005/0181012 A1 | 8/2005 | Saint et al. |
| 2005/0182306 A1 | 8/2005 | Sloan |
| 2005/0182366 A1 | 8/2005 | Vogt et al. |
| 2005/0182451 A1 | 8/2005 | Griffin et al. |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0203461 A1 | 9/2005 | Flaherty et al. |
| 2005/0214892 A1 | 9/2005 | Kovatchev et al. |
| 2005/0215871 A1 | 9/2005 | Feldman et al. |
| 2005/0215872 A1 | 9/2005 | Berner et al. |
| 2005/0218880 A1 | 10/2005 | Ioffe |
| 2005/0235732 A1 | 10/2005 | Rush |
| 2005/0238503 A1 | 10/2005 | Rush et al. |
| 2005/0238507 A1 | 10/2005 | DiIanni et al. |
| 2005/0239154 A1 | 10/2005 | Feldman et al. |
| 2005/0239518 A1 | 10/2005 | D'Agostino et al. |
| 2005/0245795 A1 | 11/2005 | Goode, Jr. et al. |
| 2005/0245799 A1 | 11/2005 | Brauker et al. |
| 2005/0249506 A1 | 11/2005 | Fuse |
| 2005/0249606 A1 | 11/2005 | Rush |
| 2005/0251083 A1 | 11/2005 | Carr-Brendel et al. |
| 2005/0261660 A1 | 11/2005 | Choi |
| 2005/0267550 A1 | 12/2005 | Hess et al. |
| 2005/0267780 A1 | 12/2005 | Ray et al. |
| 2005/0271546 A1 | 12/2005 | Gerber et al. |
| 2005/0271547 A1 | 12/2005 | Gerber et al. |
| 2005/0272640 A1 | 12/2005 | Doyle, III et al. |
| 2005/0272985 A1 | 12/2005 | Kotulla et al. |
| 2005/0277844 A1 | 12/2005 | Strother et al. |
| 2005/0287620 A1 | 12/2005 | Heller et al. |
| 2006/0001538 A1 | 1/2006 | Kraft et al. |
| 2006/0001550 A1 | 1/2006 | Mann et al. |
| 2006/0001551 A1 | 1/2006 | Kraft et al. |
| 2006/0003398 A1 | 1/2006 | Heller et al. |
| 2006/0004271 A1 | 1/2006 | Peyser et al. |
| 2006/0007017 A1 | 1/2006 | Mann et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0025663 A1 | 2/2006 | Talbot et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0036187 A1 | 2/2006 | Vos et al. |

| Publication No. | Date | Inventor |
|---|---|---|
| 2006/0040402 A1 | 2/2006 | Brauker et al. |
| 2006/0041229 A1 | 2/2006 | Garibotto et al. |
| 2006/0052679 A1 | 3/2006 | Kotulla et al. |
| 2006/0058602 A1 | 3/2006 | Kwiatkowski et al. |
| 2006/0058627 A1 | 3/2006 | Flaherty et al. |
| 2006/0063218 A1 | 3/2006 | Bartkowiak et al. |
| 2006/0074564 A1 | 4/2006 | Bartkowiak et al. |
| 2006/0094986 A1 | 5/2006 | Neel et al. |
| 2006/0161078 A1 | 7/2006 | Schraga |
| 2006/0166629 A1 | 7/2006 | Reggiardo |
| 2006/0173259 A1 | 8/2006 | Flaherty et al. |
| 2006/0173444 A1 | 8/2006 | Choy et al. |
| 2006/0178633 A1 | 8/2006 | Garibotto et al. |
| 2006/0222566 A1 | 10/2006 | Brauker et al. |
| 2006/0224141 A1 | 10/2006 | Rush et al. |
| 2006/0240403 A1 | 10/2006 | List et al. |
| 2006/0247508 A1 | 11/2006 | Fennell |
| 2006/0253085 A1 | 11/2006 | Geismar et al. |
| 2006/0273759 A1 | 12/2006 | Reggiardo |
| 2006/0282290 A1 | 12/2006 | Flaherty et al. |
| 2007/0016381 A1 | 1/2007 | Kamath et al. |
| 2007/0078323 A1 | 4/2007 | Reggiardo et al. |
| 2007/0106135 A1 | 5/2007 | Sloan |
| 2007/0118405 A1 | 5/2007 | Campbell et al. |
| 2007/0135697 A1 | 6/2007 | Reggiardo |
| 2007/0163880 A1 | 7/2007 | Woo et al. |
| 2007/0173711 A1 | 7/2007 | Shah et al. |
| 2007/0176867 A1 | 8/2007 | Reggiardo et al. |
| 2007/0203966 A1 | 8/2007 | Brauker et al. |
| 2007/0219480 A1 | 9/2007 | Kamen et al. |
| 2007/0219597 A1 | 9/2007 | Kamen et al. |
| 2007/0235331 A1 | 10/2007 | Simpson et al. |
| 2008/0021666 A1 | 1/2008 | Goode, Jr. et al. |
| 2008/0033254 A1 | 2/2008 | Kamath et al. |
| 2008/0045824 A1 | 2/2008 | Tapsak et al. |
| 2008/0064941 A1 | 3/2008 | Funderburk et al. |
| 2008/0071156 A1 | 3/2008 | Brister et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0103447 A1 | 5/2008 | Reggiardo et al. |
| 2008/0108942 A1 | 5/2008 | Brister et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0189051 A1 | 8/2008 | Goode et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0200838 A1 | 8/2008 | Goldberger et al. |
| 2008/0208025 A1 | 8/2008 | Shults et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0242961 A1 | 10/2008 | Brister et al. |
| 2008/0257063 A1 | 10/2008 | Rush et al. |
| 2008/0262469 A1 | 10/2008 | Brister et al. |
| 2008/0267787 A1 | 10/2008 | Rush et al. |
| 2008/0275313 A1 | 11/2008 | Brister et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0012379 A1 | 1/2009 | Goode et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0062633 A1 | 3/2009 | Brauker et al. |
| 2009/0062635 A1 | 3/2009 | Brauker et al. |
| 2009/0063402 A1 | 3/2009 | Hayter |
| 2009/0068954 A1 | 3/2009 | Reggiardo et al. |
| 2009/0076356 A1 | 3/2009 | Simpson et al. |
| 2009/0076358 A1 | 3/2009 | Reggiardo et al. |
| 2009/0076360 A1 | 3/2009 | Brister et al. |
| 2009/0076361 A1 | 3/2009 | Kamath et al. |
| 2009/0083003 A1 | 3/2009 | Reggiardo et al. |
| 2009/0099436 A1 | 4/2009 | Brister et al. |
| 2009/0105647 A1 | 4/2009 | Rush et al. |
| 2009/0105648 A1 | 4/2009 | Rush et al. |
| 2009/0105649 A1 | 4/2009 | Rush et al. |
| 2009/0112156 A1 | 4/2009 | Rush et al. |
| 2009/0112165 A1 | 4/2009 | Rush et al. |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0163869 A1 | 6/2009 | Rush et al. |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0287073 A1 | 11/2009 | Boock et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0008794 A1 | 1/2010 | Rush et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0019721 A1 | 1/2010 | Reggiardo |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |

| | | | |
|---|---|---|---|
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0049130 A1 | 2/2010 | Rush et al. |
| 2010/0049131 A1 | 2/2010 | Rush et al. |
| 2010/0049132 A1 | 2/2010 | Rush et al. |
| 2010/0049133 A1 | 2/2010 | Rush et al. |
| 2010/0057007 A1 | 3/2010 | Rush et al. |
| 2010/0057038 A1 | 3/2010 | Rush et al. |
| 2010/0063373 A1 | 3/2010 | Kamath et al. |
| 2010/0063446 A1 | 3/2010 | Rush et al. |
| 2010/0063449 A1 | 3/2010 | Rush et al. |
| 2010/0068072 A1 | 3/2010 | Rush et al. |
| 2010/0076283 A1 | 3/2010 | Simpson et al. |
| 2010/0076371 A1 | 3/2010 | Rush et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0100041 A1 | 4/2010 | Rush et al. |
| 2010/0100042 A1 | 4/2010 | Rush et al. |
| 2010/0114028 A1 | 5/2010 | Rush et al. |
| 2010/0114029 A1 | 5/2010 | Rush et al. |
| 2010/0114073 A1 | 5/2010 | Rush et al. |
| 2010/0119693 A1 | 5/2010 | Tapsak et al. |
| 2010/0121169 A1 | 5/2010 | Petisce et al. |
| 2010/0241076 A1 | 9/2010 | Rush et al. |
| 2010/0312177 A1 | 12/2010 | Rush et al. |

FOREIGN PATENT DOCUMENTS

| | | |
|---|---|---|
| EP | 0518524 | 12/1992 |
| EP | 0878707 | 11/1998 |
| EP | 0543916 | 7/2001 |
| EP | 1130638 | 9/2001 |
| EP | 1755443 | 11/2005 |
| EP | 1783536 | 5/2007 |
| JP | 2001-177423 | 6/2001 |
| JP | 2001-056673 | 11/2001 |
| WO | WO-96/14026 | 5/1996 |
| WO | WO-99/22236 | 5/1999 |
| WO | WO-01/52727 | 7/2001 |
| WO | WO-01/71186 | 9/2001 |
| WO | WO-02/39086 | 5/2002 |
| WO | WO-02/084860 | 10/2002 |
| WO | WO-02/100263 | 12/2002 |
| WO | WO-02/100469 | 12/2002 |
| WO | WO-03/006091 | 1/2003 |
| WO | WO-2004/028337 | 4/2004 |
| WO | WO-2004/032994 | 4/2004 |
| WO | WO-2004/061420 | 7/2004 |
| WO | WO-2005/089103 | 9/2005 |
| WO | WO-2005/101994 | 11/2005 |
| WO | WO-2006/003919 | 1/2006 |
| WO | WO-2006/079114 | 7/2006 |
| WO | WO-2006/086701 | 8/2006 |
| WO | WO-2006/102412 | 9/2006 |
| WO | WO-2006/110913 | 10/2006 |
| WO | WO-2006/113408 | 10/2006 |
| WO | WO-2006/113521 | 10/2006 |
| WO | WO-2006/118947 | 11/2006 |
| WO | WO-2006/132884 | 12/2006 |
| WO | WO-2007/041072 | 4/2007 |
| WO | WO-2007/090037 | 8/2007 |
| WO | WO-2008/055037 | 5/2008 |
| WO | WO-2008/110267 | 9/2008 |

OTHER PUBLICATIONS

Abstract of Japanese Publication No. JP-2001-077423, Published Mar. 23, 2001.
Barbosa, R. M., et al., "Electrochemical Studies of Zinc in Zinc-Insulin Solution", *Journal of the Royal Society of Chemistry, Analyst*, vol. 121, No. 12, 1996, pp. 1789-1793.
Bard, A. J., et al., "Methods Involving Forced Convection—Hydrodynamic Methods", *Electrochemical Methods—Fundamentals and Applications*, 2001, pp. 331-367.
Kissinger, P. T., "Introduction to Analog Instrumentation", *Laboratory Techniques in Electroanalytical Chemistry, Second Edition, Revised and Expanded*, 1996, pp. 165-194.
Ursino, M, et al., "A Mathematical Model of Cerebral Blood Flow Chemical Regulation—Part I: Diffusion Processes", *IEEE Transactions on Biomedical Engineering*, vol. 36, No. 2, 1989, pp. 183-191.
U.S. Appl. No. 11/145,048, Notice of Allowance mailed Sep. 21, 2009.
U.S. Appl. No. 11/145,048, Office Action mailed Apr. 11, 2008.
U.S. Appl. No. 11/145,048, Office Action mailed Apr. 3, 2009.
U.S. Appl. No. 11/145,048, Office Action mailed Jul. 16, 2007.
U.S. Appl. No. 11/145,048, Office Action mailed Oct. 29, 2008.
U.S. Appl. No. 12/571,360, Office Action mailed Jul. 9, 2010.
U.S. Appl. No. 12/571,360, Office Action mailed Feb. 2, 2011.
European Patent Application No. 06760592.3, Extended European Search Report mailed Nov. 23, 2009.
PCT Application No. PCT/US2006/021113, International Preliminary Report on Patentability and Written Opinion of the International Searching Authority mailed Dec. 21, 2007.
PCT Application No. PCT/US2006/021113, International Search Report and Written Opinion of the International Searching Authority mailed Aug. 27, 2007.

METHOD AND APPARATUS FOR PROVIDING RECHARGEABLE POWER IN DATA MONITORING AND MANAGEMENT SYSTEMS

RELATED APPLICATIONS

This application is a divisional application of pending U.S. patent application Ser. No. 11/145,048 filed Jun. 3, 2005 entitled "Method And Apparatus For Providing Rechargeable Power In Data Monitoring And Management Systems", the disclosure of which is herein incorporated by reference for all purposes.

BACKGROUND

The present invention relates to data monitoring and management systems. More specifically, the present invention relates to a method and apparatus for providing rechargeable power used in data monitoring systems such as glucose monitoring systems.

Glucose monitoring systems including continuous and discrete monitoring systems generally include a small, lightweight battery powered and microprocessor controlled system which is configured to detect signals proportional to the corresponding measured glucose levels using an electrometer, and RF signals to transmit the collected data. One aspect of such glucose monitoring systems include a sensor configuration which is, for example, mounted on the skin of a subject whose glucose level is to be monitored. The sensor cell may use a three-electrode (work, reference and counter electrodes) configuration driven by a controlled potential (potentiostat) analog circuit connected through a contact system.

The battery providing power to the microprocessor controlled system is typically configured for a limited duration usage, and thus would require periodic replacement. Furthermore, given the compact size of the system, as well as the need for water tight seals, it is not desirable to have removable components such as battery covers or additional electrical contacts that may be exposed to the environment or to the patient's skin without the addition of seals and covers.

In view of the foregoing, it would be desirable to have an approach to readily and easily provide rechargeable power to the battery in the microprocessor controlled system.

SUMMARY OF THE INVENTION

In view of the foregoing, in accordance with the various embodiments of the present invention, there is provided a method and apparatus for charging the battery through the existing analog electrical contacts (electrodes) using the electrostatic discharge (ESD) protection circuitry.

More specifically, in one embodiment of the present invention, using the guard and the counter electrodes coupled to the transmitter unit of the data monitoring and management system, the power supply of the transmitter unit may be recharged so that the power supply need not be repeatedly replenished when it has been depleted of power and can not support reliable system operation.

DETAILED DESCRIPTION

Figure 1:
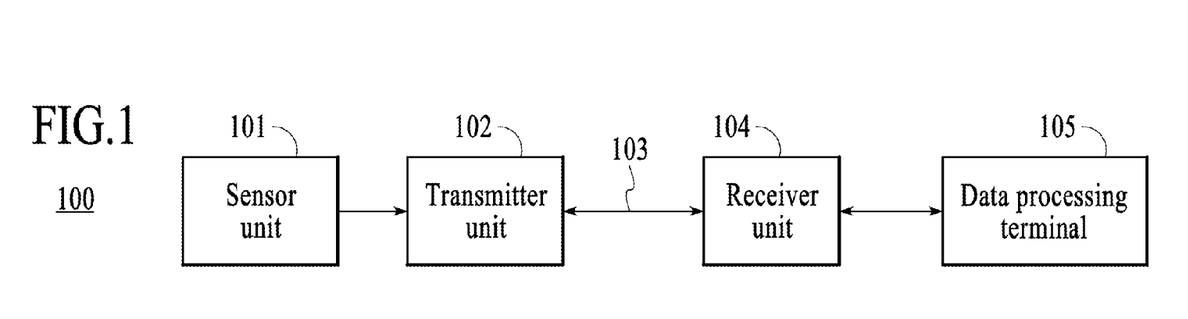
FIG. 1 illustrates a block diagram of a data monitoring and management system for practicing one embodiment of the present invention.

FIG. 1 illustrates a data monitoring and management system such as, for example, a glucose monitoring system 100 in accordance with one embodiment of the present invention. In such embodiment, the glucose monitoring system 100 includes a sensor 101, a transmitter 102 coupled to the sensor 101, and a receiver 104 which is configured to communicate with the transmitter 102 via a communication link 103. The receiver 104 may be further configured to transmit data to a data processing terminal 105 for evaluating the data received by the receiver 104. Only one sensor 101, transmitter 102, communication link 103, receiver 104, and data processing terminal 105 are shown in the embodiment of the glucose monitoring system 100 illustrated in FIG. 1. However, it will be appreciated by one of ordinary skill in the art that the glucose monitoring system 100 may include one or more sensor 101, transmitter 102, communication link 103, receiver 104, and data processing terminal 105, where each receiver 104 is uniquely synchronized with a respective transmitter 102. Moreover, within the scope of the present invention, the glucose monitoring system 100 may be a continuous monitoring system, or a semi-continuous or discrete monitoring system.

In one embodiment of the present invention, the sensor 101 is physically positioned on the body of a user whose glucose level is being monitored. The sensor 101 may be configured to continuously sample the glucose level of the user and convert the sampled glucose level into a corresponding data signal for transmission by the transmitter 102. In one embodiment, the transmitter 102 is mounted on the sensor 101 so that both devices are positioned on the user's body. The transmitter 102 performs data processing such as filtering and encoding on data signals, each of which corresponds to a sampled glucose level of the user, for transmission to the receiver 104 via the communication link 103.

In one embodiment, the glucose monitoring system 100 is configured as a one-way RF communication path from the transmitter 102 to the receiver 104. In such embodiment, the transmitter 102 transmits the sampled data signals received from the sensor 101 without acknowledgement from the receiver 104 that the transmitted sampled data signals have been received. For example, the transmitter 102 may be configured to transmit the encoded sampled data signals at a fixed rate (e.g., at one minute intervals) after the completion of the initial power on procedure. Likewise, the receiver 104 may be configured to detect such transmitted encoded sampled data signals at predetermined time intervals. Alternatively, the glucose monitoring system 10 may be configured with a bi-directional RF communication between the transmitter 102 and the receiver 104.

Additionally, in one aspect, the receiver 104 may include two sections. The first section is an analog interface section that is configured to communicate with the transmitter 102 via the communication link 103. In one embodiment, the analog interface section may include an RF receiver and an antenna for receiving and amplifying the data signals from the transmitter 102, which are thereafter, demodulated with a local oscillator and filtered through a band-pass filter. The second section of the receiver 104 is a data processing section which is configured to process the data signals received from the transmitter 102 such as by performing data decoding, error detection and correction, data clock generation, and data bit recovery.

In operation, upon completing the power-on procedure, the receiver 104 is configured to detect the presence of the transmitter 102 within its range based on, for example, the strength of the detected data signals received from the transmitter 102 or a predetermined transmitter identification information. Upon successful synchronization with the corresponding transmitter 102, the receiver 104 is configured to begin receiving from the transmitter 102 data signals corresponding to the user's detected glucose level. More specifically, the receiver 104 in one embodiment is configured to perform synchronized time hopping with the corresponding synchronized transmitter 102 via the communication link 103 to obtain the user's detected glucose level.

Referring again to FIG. 1, the data processing terminal 105 may include a personal computer, a portable computer such as a laptop or a handheld device (e.g., personal digital assistants (PDAs)), and the like, each of which may be configured for data communication with the receiver via a wired or a wireless connection. Additionally, the data processing terminal 105 may further be connected to a data network (not shown) for storing, retrieving and updating data corresponding to the detected glucose level of the user.

Within the scope of the present invention, the data processing terminal 105 may include an infusion device such as an insulin infusion pump, which may be configured to administer insulin to patients, and which is configured to communicate with the receiver unit 104 for receiving, among others, the measured glucose level. Alternatively, the receiver unit 104 may be configured to integrate an infusion device therein so that the receiver unit 104 is configured to administer insulin therapy to patients, for example, for administering and modifying basal profiles, as well as for determining appropriate boluses for administration based on, among others, the detected glucose levels received from the transmitter 102.

Figure 2:
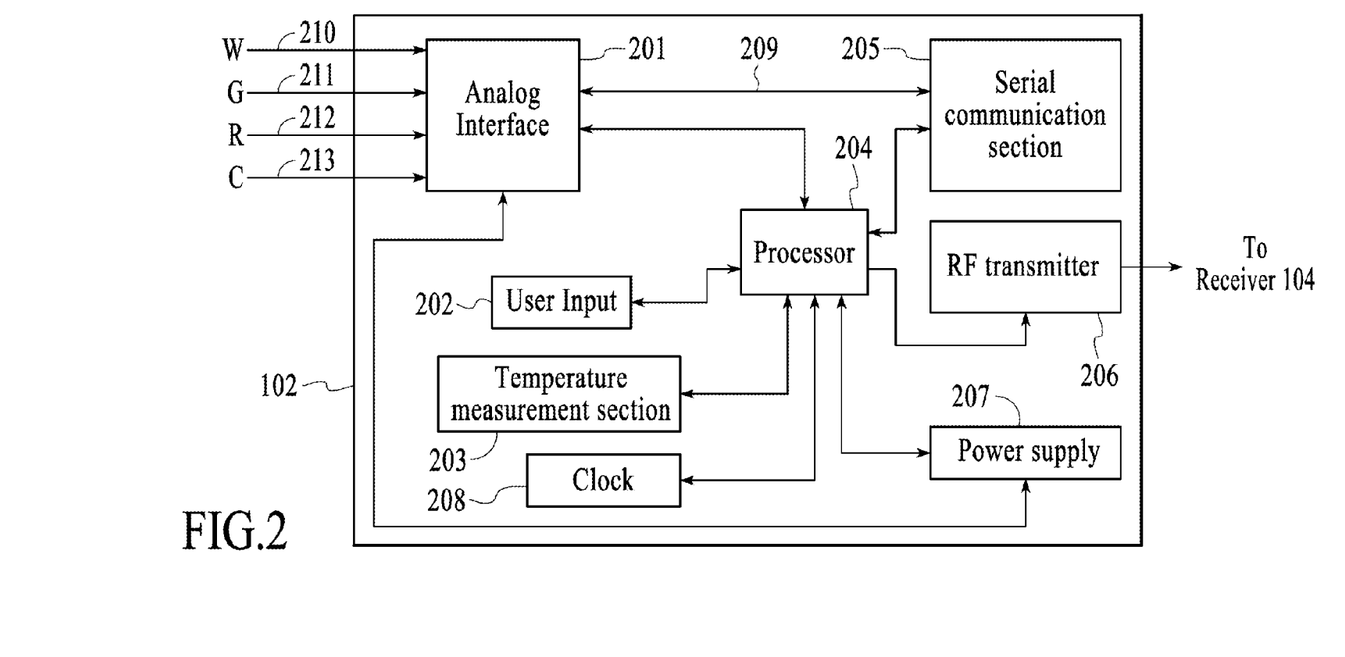
FIG. 2 is a block diagram of the transmitter of the data monitoring and management system shown in FIG. 1 in accordance with one embodiment of the present invention.

FIG. 2 is a block diagram of the transmitter of the data monitoring and detection system shown in FIG. 1 in accordance with one embodiment of the present invention. Referring to the Figure, the transmitter 102 in one embodiment includes an analog interface 201 configured to communicate with the sensor 101 (FIG. 1), a user input 202, and a temperature detection section 203, each of which is operatively coupled to a transmitter processor 204 such as a central processing unit (CPU). As can be seen from FIG. 2, there are provided four contacts, three of which are electrodes—work electrode (W) 210, guard contact (G) 211, reference electrode (R) 212, and counter electrode (C) 213, each operatively coupled to the analog interface 201 of the transmitter 102 for connection to the sensor unit 201 (FIG. 1). In one embodiment, each of the work electrode (W) 210, guard contact (G) 211, reference electrode (R) 212, and counter electrode (C) 213 may be made using a conductive material that is either printed or etched, for example, such as carbon which may be printed, or metal foil (e.g., gold) which may be etched.

Further shown in FIG. 2 are a transmitter serial communication section 205 and an RF transmitter 206, each of which is also operatively coupled to the transmitter processor 204. Moreover, a power supply 207 such as a battery, including a rechargeable battery, is also provided in the transmitter 102 to provide the necessary power for the transmitter 102 where the guard contact (G) 211 and the counter electrode (C) 213 are configured to couple to the power supply 207 through ESD clamp diodes (in the analog interface 201). Additionally, as can be seen from the Figure, clock 208 is provided to, among others, supply real time information to the transmitter processor 204. As discussed in further detail below, the power supply 207 may be configured to be recharged via a select pair of the plurality of electrodes 210-213 such as the guard contact 211 and counter electrode 213, when the transmitter unit 102 is not mounted to a patient and configured for periodic transmission of measured data to the receiver unit 103. As further discussed below, the power supply 207 may be coupled or docked to a battery charging station or unit during the recharge process, where the power supply 207 is recharged and, thereafter, when the transmitter unit 102 is mounted to the patient and coupled to the sensor 101, the power supply 207 may be configured to provide the necessary power to reliably operate the transmitter unit 102.

Referring back to the Figures, in one embodiment, a unidirectional input path is established from the sensor 101 (FIG. 1) and/or manufacturing and testing equipment to the analog interface 201 of the transmitter 102, while a unidirectional output is established from the output of the RF transmitter 206 of the transmitter 102 for transmission to the receiver 104. In this manner, a data path is shown in FIG. 2 between the aforementioned unidirectional input and output via a dedicated link 209 from the analog interface 201 to serial communication section 205, thereafter to the processor 204, and then to the RF transmitter 206. As such, in one embodiment, via the data path described above, the transmitter 102 is configured to transmit to the receiver 104 (FIG. 1), via the communication link 103 (FIG. 1), processed and encoded data signals received from the sensor 101 (FIG. 1). Additionally, the unidirectional communication data path between the analog interface 201 and the RF transmitter 206 discussed above allows for the configuration of the transmitter 102 for operation upon completion of the manufacturing process as well as for direct communication for diagnostic and testing purposes.

As discussed above, the transmitter processor 204 is configured to transmit control signals to the various sections of the transmitter 102 during the operation of the transmitter 102. In one embodiment, the transmitter processor 204 also includes a memory (not shown) for storing data such as the identification information for the transmitter 102, as well as the data signals received from the sensor 101. The stored information may be retrieved and processed for transmission to the receiver 104 under the control of the transmitter processor 204. Furthermore, the power supply 207 may include a commercially available non-rechargeable battery or a proprietary or commercially available rechargeable battery.

The transmitter 102 is also configured such that the power supply section 207 does not significantly affect the battery life after having been stored for 18 months in a low-power (non-operating) mode. In one embodiment, this may be achieved by the transmitter processor 204 operating in low power modes in the non-operating state, for example, drawing no more than approximately 1 μA of current. Indeed, in one embodiment, the final step during the manufacturing process of the transmitter 102 may place the transmitter 102 in the lower power, non-operating state (i.e., post-manufacture sleep mode). In this manner, the shelf life of the transmitter 102 may be significantly improved.

Referring yet again to FIG. 2, the temperature detection section 203 of the transmitter 102 is configured to monitor the temperature of the skin near the sensor insertion site. The temperature reading is used to adjust the glucose readings obtained from the analog interface 201. The RF transmitter 206 of the transmitter 102 may be configured for operation in the frequency band of 315 MHz to 322 MHz, for example, in the United States. Further, in one embodiment, the RF transmitter 206 is configured to modulate the carrier frequency by performing Frequency Shift Keying and Manchester encoding. In one embodiment, the data transmission rate is 19,200 symbols per second, with a minimum transmission range for communication with the receiver 104.

Additional detailed description of the continuous glucose monitoring system, its various components including the functional descriptions of the transmitter are provided in U.S. Pat. No. 6,175,752 issued Jan. 16, 2001 entitled "Analyte Monitoring Device and Methods of Use", and in application Ser. No. 10/745,878 filed Dec. 26, 2003 entitled "Continuous Glucose Monitoring System and Methods of Use", each assigned to the Assignee of the present application, and the disclosures of each of which are incorporated herein by reference for all purposes.

Figure 3:
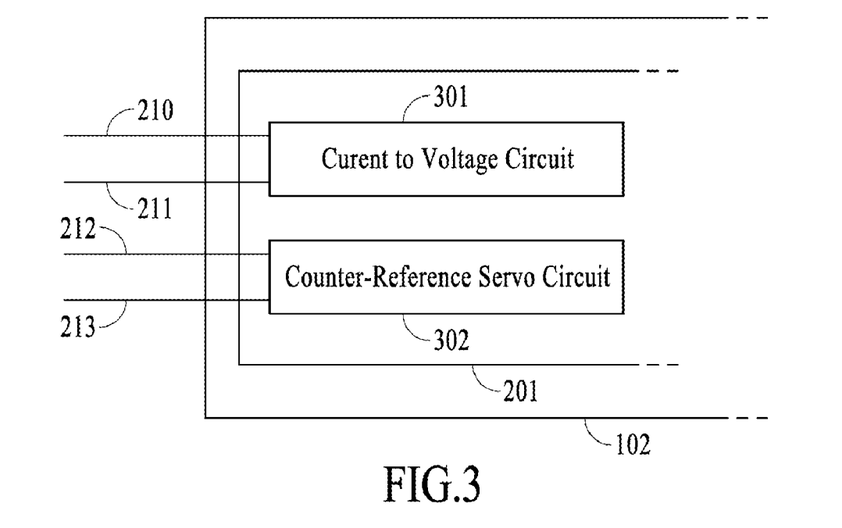
FIG. 3 illustrates the front end section of the analog interface of the transmitter in accordance with one embodiment of the present invention.

FIG. 3 illustrates the front end section of the analog interface of the transmitter in accordance with one embodiment of the present invention. Referring to the Figure, the front end section of the analog interface 201 includes a current to voltage circuit 301 which is configured to operatively couple to the work electrode 210 and the guard contact 211, and a counter-reference servo circuit 302 which is configured to operatively couple to the reference electrode 212 and the counter electrode 213.

Figure 4A:
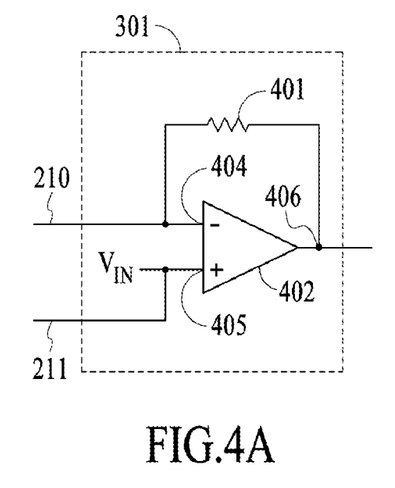
FIGS. 4A-4B respectively show detailed illustrations of the current to voltage circuit and the counter-reference servo circuit of the analog interface shown in FIG. 3 in accordance with one embodiment of the present invention.
Figure 4B:
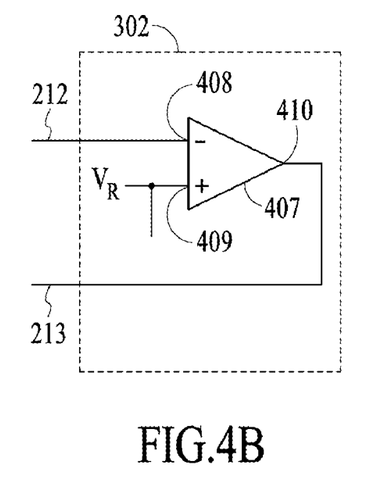

FIGS. 4A-4B illustrate detailed illustrations of the current to voltage circuit and the counter-reference servo circuit, respectively, of the analog interface shown in FIG. 3 in accordance with one embodiment of the present invention. Referring to FIG. 4A, the current to voltage circuit 301 (FIG. 3) in one embodiment includes an operational amplifier 402 having a non-inverting input terminal 405, and an inverting input terminal 404. Also shown in the Figure is a resistor 401 operatively coupled to the inverting input terminal 404 of the operational amplifier 402, and an output terminal 406.

Referring again to FIG. 4A, the work electrode 210 is operatively coupled to the inverting input terminal 404 of the operational amplifier 402, while the guard contact 211 is operatively coupled to the non-inverting input terminal 405 of the operational amplifier 402. It can be further seen that the work voltage source Vw is provided to the non-inverting terminal 405 of the operational amplifier 402. In this manner, in accordance with one embodiment of the present invention, a separate contact, the guard contact 211 is operatively coupled to the analog interface 201 (FIG. 2) of the transmitter 102 (FIG. 2). The guard contact 211 is provided at a substantially equipotential to the work electrode 210 such that any current leakage path to the work electrode 210 (from either the reference electrode 212 or the counter electrode 213, for example) is protected by the guard contact 211 by maintaining the guard contact 211 at substantially the same potential as the work electrode 210.

Referring now to FIG. 4B, the counter-reference servo unit 302 in accordance with one embodiment includes an operational amplifier 407 having an inverting input terminal 408 and a non-inverting input terminal 409, as well as an output terminal 410. In one embodiment, the reference electrode 212 is operatively coupled to the inverting input terminal 408, while the counter electrode 213 is operatively coupled to the output terminal 410 of the operational amplifier 407 in the counter-reference servo unit 302. It can also be seen from FIG. 4B that a reference voltage source Vr is provided to the non-inverting input terminal 409 of the operational amplifier 407 in the counter-reference servo unit 302.

Referring back to FIGS. 3 and 4A-4B, in accordance with one embodiment of the present invention, the current to voltage circuit 301 and the counter-reference servo unit 302 are operatively coupled to the remaining sections of the analog interface 201 of the transmitter 102, and configured to convert the detected glucose level at the sensor unit 101 (FIG. 1) into an analog signal for further processing in the transmitter unit 102. It should also be noted that, in the manner described, the Poise voltage (for example, at a value of 40 mV) may be determined based on the difference between the voltage signal level of the work voltage source Vw at the non-inverting input terminal 405 of the operational amplifier 402 in the current to voltage circuit 301, and the voltage signal level of the reference voltage source Vr at the non-inverting input terminal 409 of the operational amplifier 407 in the counter-reference servo unit 302.

Figure 5:
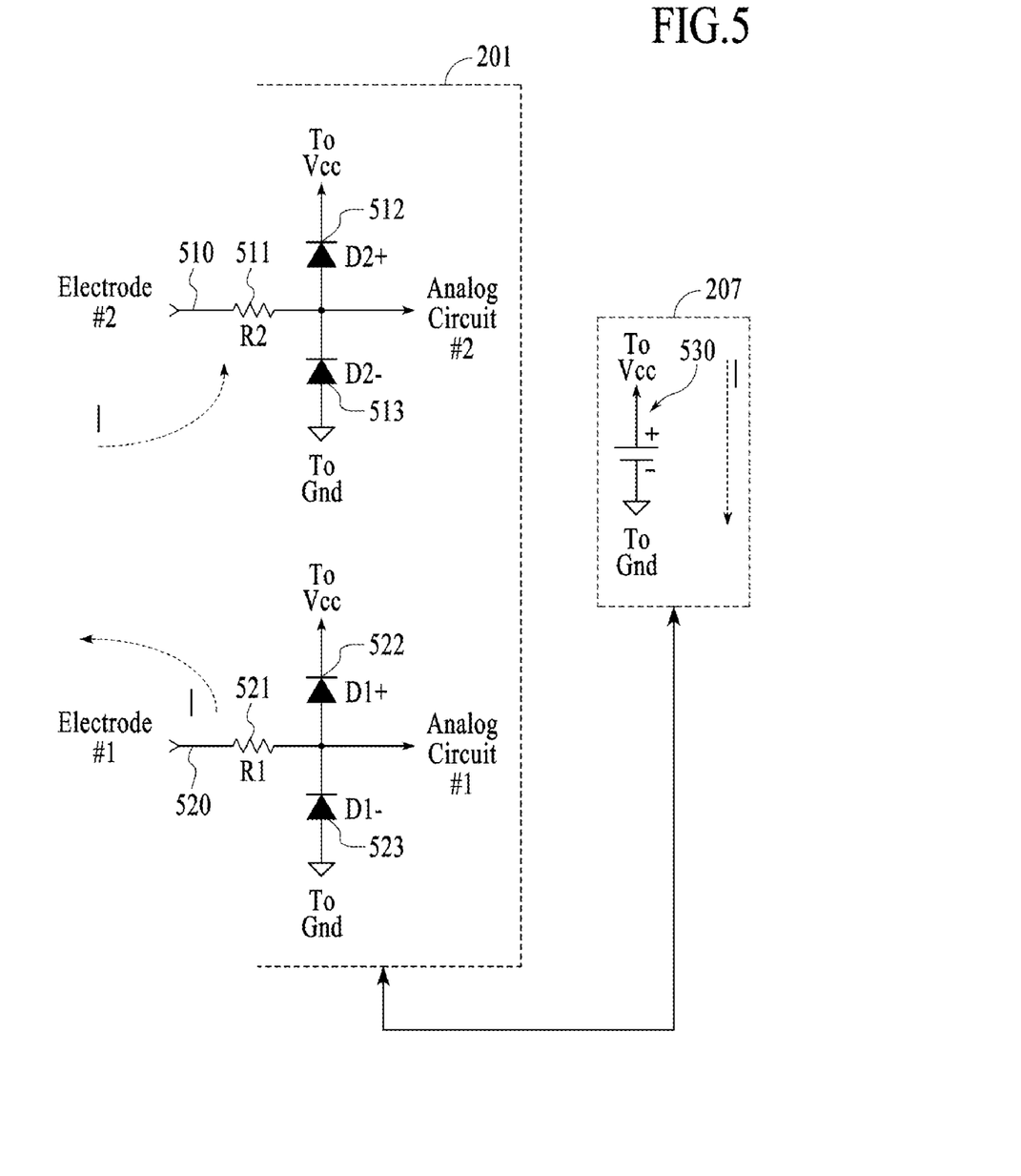
FIG. 5 illustrates the battery recharging circuit in accordance with one embodiment of the present invention.

FIG. 5 illustrates the battery recharging circuit in accordance with one embodiment of the present invention. Referring to the Figure, in one embodiment of the present invention, the analog interface unit 201 of the transmitter unit 102 includes a pair of electrode contacts 510, 520 which are configured to respectively couple to the electrode contacts of the transmitter unit 102 for example, to the electrode contacts for the guard contact 211 and the counter electrode 213 (FIG. 3). Within the scope of the present invention, the guard contact 211 in one embodiment may not be configured as an electrode with respect to the sensor unit 101, but referred to herein as an electrode. The electrode contact 510 which, in one embodiment is coupled to the counter electrode 213 contact of the transmitter unit 102, for example, is coupled in series to a resistor 511 that is in turn, further coupled to a pair of ESD protection diodes 512, 513. Moreover, in one embodiment, the electrode contact 520 which in one embodiment is coupled to the guard contact 211 contact of the transmitter unit 102, is coupled in series to a resistor 521, that is in turn, further coupled to another pair of EDS protection diodes 522, 523.

In this manner, in one embodiment of the present invention, during the power supply or battery recharging process (for example, when the transmitter unit 102 is docked or positioned in the power supply recharging unit (not shown)), electrode contact 520 is coupled to the recharging unit's ground terminal potential, while the electrode contact 510 is coupled to the positive charging voltage supply. In this manner, as shown in FIG. 5, current I is configured to flow into the electrode contact 510 through resistor 511, and forward bias the ESD protection diodes 512, and 523, thereby charging the battery 530 of the power supply 207 (FIG. 2) for the transmitter unit 102, and then flow through resistor 521 out to the electrode contact 520 which is held at ground potential as discussed above. Due to symmetry, this process also works when electrode contact 510 is coupled to the recharging unit's ground terminal potential, while the electrode contact 520 is coupled to the positive charging voltage supply such that the ESD protection diodes 513, and 522 become forward biased.

In the manner described above, in one embodiment of the present invention, the current I may be monitored and the voltage drops across the resistors 511 and 521 and the respective pairs of the ESD protection diodes 512, 513, and 522, 523 may be determined (for example, based on current), so as to control the battery 530 charging voltage level and to ensure that the power supply 207 is properly charged.

Indeed, in one embodiment of the present invention, a positive charging voltage may be applied to one electrode of the transmitter unit 102 such as the counter electrode 213 with respect to another electrode such as the guard contact 211, so that current would flow into the electrode contact 510 coupled to the counter electrode 213, through the counter electrode ESD protection resistor 511, and also, through the counter electrode positive clamp diode 512, and through the battery 530 of the power supply 207 thereby charging the battery 530 of the power supply 207. Additionally, the current also flows through the guard contact negative clamp diode 523, and through the guard ESD protection resistor 521, and out the electrode contact 520 coupled to the guard contact 211. In one embodiment, the counter electrode and guard contact ESD protection resistors 511, 521 include nominal resistor values from 50 ohms to 1 Kohm.

In the embodiment described above, the counter electrode 213 and the guard contact 211 were used for the power supply 207 recharging process because they have lower ESD protection resistors (for example, at 50 Ohms to 1 Kohms nominal) as compared to the ESD protection resistors of the work electrode 210 and the reference electrode 212 which may be at 10 Kohms nominal. Moreover, the counter electrode 213 and the guard contact 211 have common clamp diodes (For example, having part No. BAV199) as compared to the low-leakage ESD protection devices that are required for the work electrode 210 and the reference electrode 212 (each of which may use STTRDPAD diodes or alternate ESD protection technology such as the SurgX0603ESDA). Moreover, they have series resistors (10 K nominal) between the clamp diode (ESD protection device) node and the driving circuits.

Although both the counter electrode 213 and the guard contact 211 signals are outputs, in one embodiment, each has a series resistor (for example, 20 Kohms nominal) between the ESD diode clamp node and the associated analog circuitry (not shown) making it is acceptable to overdrive each of these signals with the charging voltage without causing damage.

Moreover, it should be noted that the charging voltage to the power supply charging unit should be limited to 3.6 volts or less to prevent potential damage to the battery 530 and the transmitter unit 102 circuitry during the recharging process. The voltage limit of 3.6 Volts in one embodiment is the voltage limit of the processor 204 of the transmitter unit 102. For example, if the battery 530 is being recharged with a 10 mA current and the voltage across the ESD protection resistors 511 and 521 is modeled as 1 volt each (assuming 100 ohm valued resistors) and the voltage across the ESD protection diodes 512 and 523 is modeled as 0.7 volts each (assuming BAV199 part numbers), then the charging circuit would limit the charging voltage to 7 volts, which is a sum of the voltages across the ESD protection resistors 511, 521, the voltages across the two ESD protection diodes 512, 523, and the voltage limit of the processor 204.

Moreover, while the counter electrode 213 and the guard contact 211 are used for the power supply 207 recharging process in the embodiment discussed above, within the scope of the present invention, the work electrode 210 and the reference electrode 212 may be used for the power supply 207 charging process.

Additionally, within the scope of the present invention, if the comparator used for data input through the analog front end (AFE) was maintained, then the comparator may be configured to toggle when the transmitter unit 102 is docked or coupled to the power supply charging unit, thus effectively, pulling the electrode contact 520 coupled to the guard contact 211 in one embodiment low with respect to the electrode contact 510 coupled in one embodiment to the counter electrode 213, and further, to revert when the transmitter unit 102 is undocked or removed from the power supply charging unit.

In this manner, within the scope of the present invention, it is possible to provide a signal representative of an indication that the transmitter unit 102 is in a recharging process, such that the power supply monitoring algorithm for example, in the processor 204 (FIG. 2) may be updated accordingly. For example, the amount of battery 530 life, which decreases with respect to usage time, may be increased with respect to charging time. This allows an accurate estimate of usable battery 530 life so that a new sensor may not be inserted when the system does not have sufficient battery life to support proper operation for the life of a given sensor 101 (FIG. 1). Moreover, this may allow normal transmitter unit 102 operation and RF transmissions to be suspended when the transmitter unit 102 is being charged to prevent RF contention or collision with a second transmitter unit that may be used when the first transmitter unit 102 is charging.

In the manner described above, in accordance with one embodiment of the present invention, to maintain the smallest possible size and cost, is a method of recharging the battery or power supply 207 of the transmitter unit 102 through the ESD protection circuitry on two of the four electrodes 210-213. Moreover, in the manner described above, in one embodiment of the present invention, the risk of having a pair of unprotected battery contacts exposed to the patient and the environment is eliminated.

Indeed, as discussed above, in accordance with the various embodiments of the present invention, when the data monitoring and management system 100 (and in particular, the transmitter unit 102) is not connected to a patient, it can be connected to a battery charging system. This battery charger would hold one of the two electrodes used for charging the battery at the chargers ground potential. The second of the two electrodes used for charging the battery would then be brought to a potential to forward bias the ESD protection diodes causing a current to flow into one electrode, through any series resistance, through an ESD protection diode to the positive battery contact, through the battery- thus charging the battery, out the negative battery contact through another ESD protection diode, through any series resistance, and out the second electrode. By monitoring the current and calculating the voltage drops across any series resistance elements and the ESD protection diodes, the battery voltage can be controlled and proper charging achieved.

Figure 6:
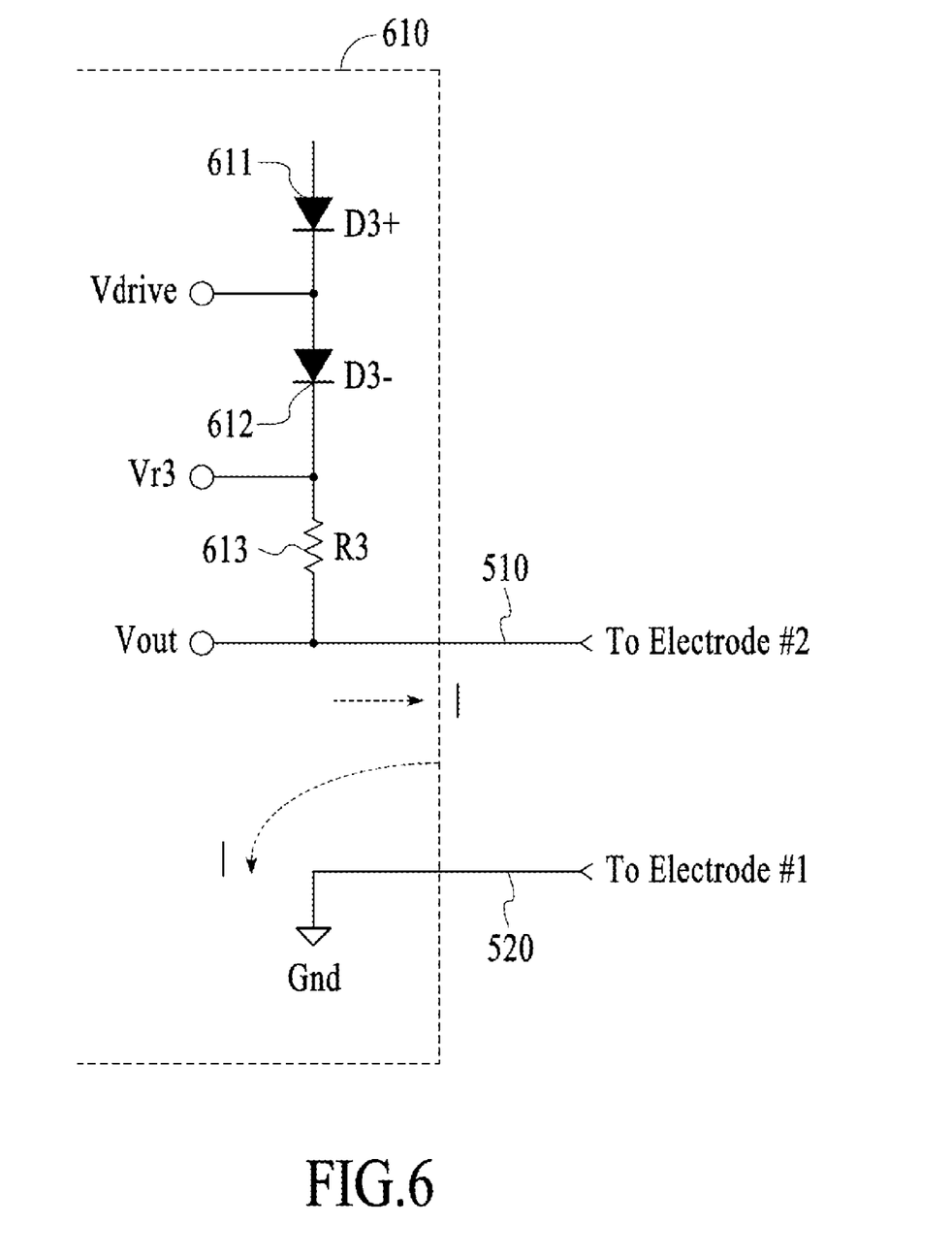
FIG. 6 illustrates the battery recharging circuit in accordance with another embodiment of the present invention.

FIG. 6 illustrates a portion of the battery recharging circuit for battery recharging through ESD protection circuitry in accordance with another embodiment of the present invention. Referring to the Figure, a battery recharging unit 610 (such as, for example, a recharging docking station) is provided with a pair of diodes 611, 612 coupled to a resistor 613 as shown in the Figure such that a current I is configured to flow from electrode contact 510, into the transmitter unit 102, and back out through the electrode contact 520, thus creating a recharging current path through the rechargeable battery 530 (for example, FIG. 5) in the transmitter unit 102 power supply 207.

While the voltage level at the electrode contact 510 (at terminal Vout shown in FIG. 5) may be driven directly, the recharging unit needs to have knowledge of the recharging voltage at the battery, and thus the recharging current through the various ESD components such as the diodes and series resistors as described above. Moreover, most batteries require recharging based on a voltage-current profile over time.

Indeed, many batteries require different voltage-current profiles for various stages of the charging process (i.e. one profile for a "fast-charge" portion up to 80% recharge and another profile for the remaining recharge portion, for example). As a result, the charging voltage is often driven through a shunt resistor 613, that is, at the drive node Vr3, with feedback to indicate the charging current and voltage (Vr3 minus Vout and Vout respectively).

In one embodiment, the battery recharging process through ESD protection circuitry may include driving node Vdrive and determining the feedback at the node Vdrive, node Vr3 and node Vout, to calculate the current into and voltage across the rechargeable battery 530, where the diode 611 and the resistor 613 are selected to match the component values of the ESD protection circuitry for the transmitter unit 102 being recharged. Thus the voltage across the diode 612 and the resistor 613 (Vdrive minus Vout) matches the voltage across the resistor 511 (FIG. 5) and the diode 512 (FIG. 5) pair and the voltage across the resistor 521 (FIG. 5) and the diode 523 (FIG. 5) pair giving the battery 530 voltage as Vout−2*(Vdrive−Vout) or 3Vout−2Vdrive.

One advantage of this approach is that there is no need to model the voltage drop across the ESD protection diodes, which are not linear with respect to current, as they match the voltage drop across the diode 612, where the diode 611 is inactive just as, for example the diode 513 (FIG. 5) and the diode 522 are inactive (there is similar component package heating as all components are used in a similar fashion).

For example, if the transmitter unit 102 being recharged uses BAV199 ESD protection diodes and 100 Ohm series resistors as described above, then the diode 611 is a BAV199 diode and the resistor 613 is 100 Ohms (the precision of which is selected as is appropriate) such that the current I=Vr3−Vout/R3 (resistor 613), which is equal to Vr3−Vout/100. The voltage at Vdrive is then driven using analog, digital (digital logic such as a microprocessor and a D/A converter) or some combination of mixed signal techniques (analog and digital) to maintain the preferred voltage-current battery recharging profile over time. Moreover, this technique allows the recharging circuitry to be larger and more complex while maintaining the small size and low cost of the unit being recharged.

Figure 7A:
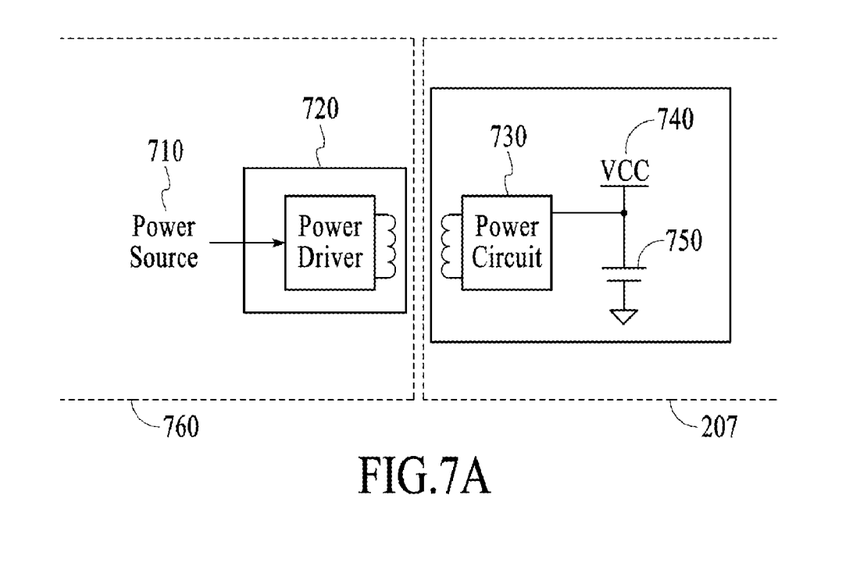
FIGS. 7A-7B illustrates inductive battery recharging in accordance with alternate embodiments of the present invention.
Figure 7B:
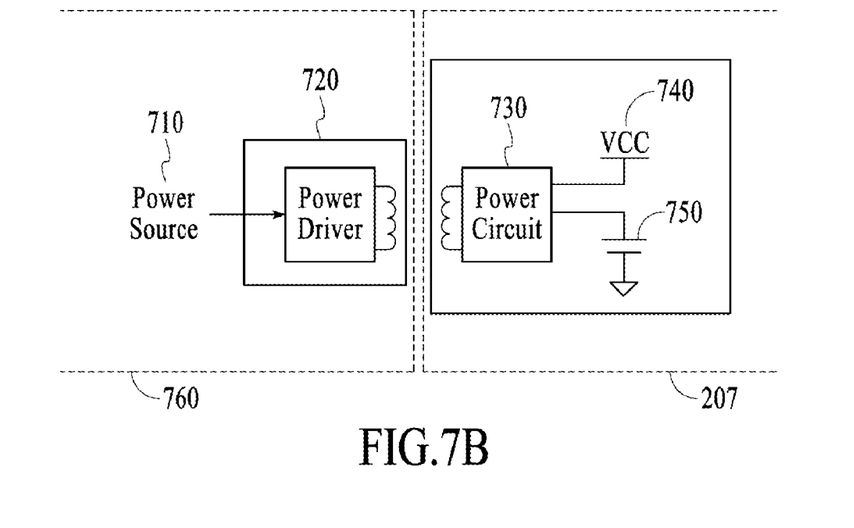

FIGS. 7A-7B illustrates inductive battery recharging in accordance with alternate embodiments of the present invention. Referring to FIG. 7A, in one embodiment of the present invention, during the power supply or battery recharging process (for example, when the transmitter unit 102 is docked or positioned in the power supply recharging unit 760), power source 710, such as a wall plug or an external battery, is coupled to a power driver 720 of the power supply recharging unit 760. As shown in the Figure, there is also provided a power circuit 730 in the power supply 207 of the transmitter unit 102 which, together with the power driver 720 comprise a transformer. As can be further seen from FIG. 7A, the power circuit 730 in the power supply 207 of the transmitter unit 102 in one embodiment may be further coupled to the power supply source 740 which is configured to supply power to the transmitter unit 102 when the transmitter is in normal operation, and further, to the rechargeable battery 750.

In this manner, in one embodiment of the present invention, the power circuit 730 of the power supply 207 in the transmitter unit 102 may be configured to recharge the battery 750 based on a predetermined and/or desired voltage-current recharging profiles whenever power is applied via the power source 710 and power driver 720.

Referring to FIG. 7B, an alternate embodiment of the inductive power supply recharging schematic is shown, where, there is also provided a separate connection to the rechargeable battery 750 coupled to the power circuit 730, and which, in one embodiment is configured to supply power to the transmitter unit 102 power supply 207 via the power supply source 740, or alternatively, be recharged by the power circuit 730 via the power source 710 when coupled thereto. When recharging, the power supply source 740 may be set to 0 Volts to disable system operation, or alternatively, may be a valid operating voltage provided by the power circuit 730. One advantage of this approach is that the power circuit 730 need not account for power being consumed by the supply source 740 when recharging the battery 750 according to the predetermined and/or desired voltage-current profiles.

In the manner described above, in accordance with one embodiment of the present invention, inductive power charging is provided using a transformer and receiving power from an external power source during the power supply or battery recharging process (for example, when the transmitter unit 102 is docked or positioned in the power supply recharging unit). Moreover, a rechargeable battery may be provided in the transmitter unit to provide power when the external power source is disconnected. Similar to the approach shown in FIG. 5 above, in one aspect of the present invention, the power circuit 730 may provide a signal representative of an indication that the transmitter unit 102 is in a recharging process, such that the power supply monitoring algorithm for example, in the processor 204 (FIG. 2) may be updated accordingly.

In this manner, within the scope of the present invention, there is provided an apparatus for recharging power in a data communication device including a plurality of contacts, a power source operatively coupled to the plurality of contacts, and a rechargeable battery operatively coupled to the plurality of contacts, where the rechargeable battery is configured to receive a predetermined signal from the power source, and further, where the rechargeable battery is configured to recharge based on the predetermined signal from the power source.

The plurality of contacts may include a guard contact and a counter electrode, and the rechargeable battery and the plurality of contacts may be provided in a data communication device, wherein the rechargeable battery is configured to provide power to the data communication device.

The data communication device in one embodiment may include a data transmitter, and the data transmitter may be configured to transmit measured glucose data. In one embodiment, the data communication device may be configured for either a uni-directional or bi-directional wireless data communication. Further, in one embodiment, the wireless data communication may include one or more of the following data communication protocols: rf communication, infrared communication, Bluetooth data communication; and 802.11x communication protocol.

In a further aspect, the transmitter may be configured to receive the measured glucose data from a sensor, where the sensor may include one of a subcutaneous sensor and a transcutaneous sensor, configured to detect an analyte level, which in one embodiment includes glucose level.

An apparatus including a rechargeable power in a glucose monitoring system in a further embodiment of the present invention includes a sensor configured to detect one or more glucose level of a patient, a transmitter unit configured to receive the one or more detected glucose levels, and to transmit one or more data corresponding to the detected one or more glucose levels, and a receiver unit configured to receive the transmitted one or more measured glucose data, where the transmitter unit includes a rechargeable battery, where the sensor includes a plurality of sensor contacts, each of the plurality of sensor contacts coupled to the transmitter unit, and further, where a pair of the plurality of sensor contacts coupled to the transmitter unit is configured to receive a predetermined power signal to charge the rechargeable batter of the transmitter unit.

In one embodiment, the pair of plurality of sensor contacts configured to receive a predetermined power signal may include a guard contact and a counter electrode, and further, where the predetermined power signal may include a current signal from a power source.

A method for recharging power in a data communication device in a further embodiment of the present invention includes the steps of providing a plurality of contacts, operatively coupling a power source to the plurality of contacts, and operatively coupling a rechargeable battery to the plurality of contacts, the rechargeable battery configured to receive a predetermined signal from the power source, where the rechargeable battery is configured to recharge based on the predetermined signal from the power source.

The method in a further embodiment may include the step of providing the rechargeable battery and the plurality of contacts in a data communication device, where the rechargeable battery is configured to provide power to the data communication device.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A glucose monitoring system including a rechargeable battery, the glucose monitoring system comprising:
   a sensor configured to detect one or more glucose levels within a patient;
   a transmitter unit configured to receive from the sensor the one or more detected glucose levels via a plurality of transmitter unit contacts, each configured for coupling to a respective one of a working electrode, a reference electrode, or a counter electrode of the sensor, and where each of the plurality of transmitter unit contacts are further configured to couple to a voltage contact and a ground contact of a charging system positioned externally to the glucose monitoring system;
   a battery recharging circuit positioned within the transmitter unit and comprising electrostatic discharge protection circuitry, and configured to operatively couple the plurality of transmitter unit contacts to the rechargeable battery; and
   a processor positioned within the transmitter unit, operatively coupled to the battery recharging circuit, and configured to generate one or more signals indicative of the rechargeable battery being recharged;
   wherein the rechargeable battery is configured to provide power to the glucose monitoring system when the plurality of transmitter unit contacts are coupled to respective contacts of the sensor; and
   wherein the plurality of transmitter unit contacts are disconnected from the sensor when the battery is being recharged by coupling the plurality of transmitter unit contacts to the charging system.

2. The glucose monitoring system of claim 1, wherein the battery recharging circuit is coupled to two of the plurality of transmitter unit contacts.

3. The glucose monitoring system of claim 2, wherein the two transmitter contacts coupled to the battery recharging circuit correspond to a guard contact and the counter electrode of the sensor.

4. The glucose monitoring system of claim 1, wherein the sensor includes one of a subcutaneous sensor or a transcutaneous sensor.

5. The glucose monitoring system of claim 1, wherein the electrostatic discharge protection circuitry comprises at least two contacts, each coupled in series to a resistor coupled to a pair of electrostatic discharge diodes.

6. The glucose monitoring system of claim 1, wherein the transmitter unit contacts configured to couple to the guard contact and the work electrode of the sensor are maintained at substantially the same electrical potential.

7. The glucose monitoring system of claim 1, further including a receiver unit configured to receive the one or more detected glucose levels from the transmitter unit.

8. The glucose monitoring system of claim 7, further including a data processing terminal for processing glucose data from the receiver unit.

9. A method of monitoring at least one glucose level of a patient, the method comprising:
   providing a sensor to detect one or more glucose levels within a patient;
   providing a transmitter unit to receive the one or more detected glucose levels from the sensor via a plurality of transmitter unit contacts, each coupled to a respective one of a working electrode, a reference electrode, or a counter electrode of the sensor, where each of the plurality of transmitter unit contacts are further coupled to a voltage contact and a ground contact of a charging system positioned externally to the glucose monitoring system;
   positioning a battery recharging circuit within the transmitter unit where the battery recharging circuit comprises electrostatic discharge protection circuitry, and operatively coupling the plurality of transmitter unit contacts to the rechargeable battery; and
   positioning a processor within the transmitter unit, operatively coupling the processor to the battery recharging circuit, and generating one or more signals indicative of the rechargeable battery being recharged;
   wherein the rechargeable battery provides power to the glucose monitoring system when the plurality of transmitter unit contacts are coupled to respective contacts of the sensor; and
   wherein the plurality of transmitter unit contacts are disconnected from the sensor when the battery is being recharged by coupling the plurality of transmitter unit contacts to the charging system.

10. The method of claim 9, further including coupling the battery recharging circuit to two of the plurality of transmitter unit contacts.

11. The method of claim 10, further including coupling the two transmitter unit contacts corresponding to a guard contact and the counter electrode sensor to the battery recharging circuit.

12. The method of claim 9, further including maintaining the transmitter unit contacts corresponding to the guard con tact and the work electrode of the sensor at substantially the same electrical potential.

13. The method of claim 9, further including providing a receiver unit to receive the one or more detected glucose levels from the transmitter unit.

14. The method of claim 13, further including providing a data processing terminal for processing glucose data from the receiver unit.

* * * * *